(12) United States Patent
Wagner et al.

(10) Patent No.: US 11,972,869 B2
(45) Date of Patent: Apr. 30, 2024

(54) SYSTEMS AND METHODS FOR DIAGNOSING A HEALTH CONDITION BASED ON PATIENT TIME SERIES DATA

(71) Applicant: Anumana, Inc., Cambridge, MA (US)

(72) Inventors: Tyler Wagner, Boston, MA (US); Murali Aravamudan, Andover, MA (US); Melwin Babu, Thrissur (IN); Rakesh Barve, Bangalore (IN); Venkataramanan Soundararajan, Andover, MA (US); Ashim Prasad, Bangalore (IN); Corinne Carpenter, Cambridge, MA (US); Katherine Carlson, Cambridge, MA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/386,056

(22) Filed: Nov. 1, 2023

(65) Prior Publication Data
US 2024/0062905 A1 Feb. 22, 2024

Related U.S. Application Data

(63) Continuation of application No. 17/552,246, filed on Dec. 15, 2021.

(60) Provisional application No. 63/156,531, filed on Mar. 4, 2021, provisional application No. 63/126,331, filed on Dec. 16, 2020.

(51) Int. Cl.
G16H 50/20 (2018.01)
G06N 3/08 (2023.01)
G16H 10/60 (2018.01)

(52) U.S. Cl.
CPC .............. G16H 50/20 (2018.01); G06N 3/08 (2013.01); G16H 10/60 (2018.01)

(58) Field of Classification Search
CPC .......... G16H 50/20; G16H 10/60; G06N 3/08
See application file for complete search history.

(56) References Cited

U.S. PATENT DOCUMENTS

2007/0273504 A1* 11/2007 Tran ..................... A61B 5/7405
340/539.12
2020/0160980 A1* 5/2020 Lyman ................... G06Q 20/14

FOREIGN PATENT DOCUMENTS

CN 107301409 A * 10/2017 ............. A61B 5/316

OTHER PUBLICATIONS

Yoo, Sun Kook; Lee, Kwanghyun; Lee, Moon H. "Empirical determination of an ECG compression ratio for mobile telecardiology applications." Telemedicine and e-Health 14.2: 156(8). Mary Ann Liebert, Inc. (Mar. 2008) (Year: 2008).*

* cited by examiner

Primary Examiner — Linh Giang Le
(74) Attorney, Agent, or Firm — Caldwell Intellectual Property Law

(57) ABSTRACT

Disclosed systems, methods, and computer readable media can diagnose a health condition based on patient time series data. For example, a method for diagnosing a health condition based on patient time series data includes identifying a training set of health records comprising a first set of patient time series data, training a neural network using the training set of health records, and executing the trained neural network model to diagnose a health condition based on a second set of patient time series data. In further examples, the first set of patient time series data and the second set of patient time series data can each comprise electrocardiogram data and the health condition can comprise pulmonary hypertension.

20 Claims, 47 Drawing Sheets

| Cohort | Positive | Unique Patients | Negative | Unique Patients |
|---|---|---|---|---|
| 1 | mPAP ≥ 25 mmHg | 11215 | mPAP < 21 mmHg | 2293 |
| 2 | mPAP ≥ 21 mmHg | 12827 | mPAP < 21 mmHg | 2293 |
| 3 | mPAP ≥ 25 mmHg | 11215 | mPAP < 21 mmHg + TRV ≤ 2.8 m/s | 50768 |
| 4 | mPAP ≥ 21 mmHg | 12827 | mPAP < 21 mmHg + TRV ≤ 2.8 m/s | 50768 |
| 5 | TRV ≥ 3.4 m/s | 15515 | TRV ≤ 2.8 m/s | 49614 |
| 6 | TRV ≥ 2.8 m/s | 39238 | TRV ≤ 2.8 m/s | 49614 |
| 7 | Echo + Clinical Notes Positive | 5994 | Echo + Clinical Notes Negative | 56835 |
| 8 | mPAP ≥ 25 mmHg | 11215 | mPAP < 21 mmHg + TRV ≤ 2.6 m/s | 41804 |
| 9 | mPAP ≥ 21 mmHg | 12827 | mPAP < 21 mmHg + TRV ≤ 2.6 m/s | 41804 |
| 10 | TRV ≥ 3.4 m/s | 15515 | TRV ≤ 2.6 m/s | 40263 |
| 11 | TRV > 2.8 m/s | 39238 | TRV ≤ 2.6 m/s | 40263 |
| 12 | mPAP > 20 mmHg + TRV > 3.4 m/s | 19422 | mPAP ≤ 20 mmHg + TRV < 2.8 m/s | 42144 |

FIG. 10A

Positive diagnosis (YES)

"In regards to Ms. [NAME]'s history of atrial fibrillation, she reports that she had occasional short episodes of a rapid rate that lasts a minute."

"He has severe tricuspid regurgitation due to a partial flail tricuspid leaflet and a history of anemia."

Suspected Diagnosis (MAYBE)

"However, this could also be due to interstitial lung diseases such as sarcoidosis, hypersensitivity pneumonitis, or Langerhans cell histiocytosis."

"Because of the swelling I wonder about the possibility of cor pulmonale and underlying pulmonary hypertension."

Negative diagnosis (NO)

"She has no history of chronic lung disease, rheumatic fever, or endocarditis."

"Although her right ventricle is compromised she is quite well compensated hemodynamically without evidence of right ventricular failure."

Alternate Context (OTHER)

"I have also sent him a copy of our recent paper on smoking related interstitial lung diseases."

"She has no family history of lung fibrosis or other lung diseases."

FIG. 10B

<u>11,433 Total Sentences</u>
- 7409 tagged as YES
- 1328 tagged as NO
- 1469 tagged as MAYBE
- 1195 tagged as OTHER

Using all classification labels
Accuracy: 0.85

| Label | Precision | Recall | F1-Score |
|---|---|---|---|
| Other | 0.67 | 0.64 | 0.66 |
| Maybe | 0.65 | 0.61 | 0.63 |
| No | 0.79 | 0.89 | 0.84 |
| Yes | 0.93 | 0.93 | 0.93 |

<u>15,121 Total Sentences</u>
- 9615 tagged as YES
- 1724 tagged as NO
- 1930 tagged as MAYBE
- 1852 tagged as OTHER

Using all classification labels
Accuracy: 0.91

| Label | Precision | Recall | F1-Score |
|---|---|---|---|
| Other | 0.81 | 0.75 | 0.78 |
| Maybe | 0.73 | 1.78 | 0.76 |
| No | 0.88 | 0.93 | 0.91 |
| Yes | 0.96 | 0.95 | 0.96 |

<u>18,490 Total Sentences</u>
- 11,505 tagged as YES
- 2265 tagged as NO
- 2236 tagged as MAYBE
- 2485 tagged as OTHER

Using all classification labels
Accuracy: 0.936

| Label | Precision | Recall | F1-Score |
|---|---|---|---|
| Other | 0.81 | 0.91 | 0.86 |
| Maybe | 0.87 | 0.83 | 0.85 |
| No | 0.97 | 0.95 | 0.96 |
| Yes | 0.97 | 0.96 | 0.96 |

FIG. 10C

| Model Name | PH -1 month to 1 month: Patient-Wise AUC | PH -1 month to 1 month: Gender-Wise AUC | PH 6 month to 18 month: Patient-Wise AUC | PH 6 month to 18 month: Gender-Wise AUC |
|---|---|---|---|---|
| Single Branch Conv 1D | 0.8625 | 0.8477 | 0.7662 | 0.7442 |
| Four Branch Conv 1D | 0.8619 | 0.8169 | 0.7735 | 0.7072 |
| 12 Branch Conv 1D | 0.8428 | 0.7906 | 0.7394 | 0.6341 |
| Spectrogram Model | 0.8390 | 0.8134 | 0.6194 | 0.6266 |

FIG. 11B

- Intuition: We need penalize errors for ECGs less from patients falling in intermediate value cohorts:
  - 2.8 m/s ≤ TRV ≤ 3.4 m/s
  - 21 mmHg < mPAP < 25 mmHg
- Intuitively, results should improve for cohorts with closer bounds
  - Cohort 2: mPAP ≥ 21 mmHg vs. mPAP < 21 mmHg
  - Cohort 6: TRV > 2.8 m/s vs. TRV ≤ 2.8 m/s
- RHC mPAP Values scaled as: $z = \dfrac{mPAP-21}{25-21}$
- Echo TRV Values scaled as: $z = \dfrac{TRV-2.8}{3.4-2.8}$

|  | Probability Encoded Model | Non-Probability Encoded Model | Probability Encoded Model | Non-Probability Encoded Model |
| --- | --- | --- | --- | --- |
|  | Patient Wise AUC | Patient Wise AUC | Age Gender Wise AUC | Age Gender Wise AUC |
| Cohort 2 Diagnostic Set | 0.71 | 0.6952 | 0.6751 | 0.6615 |
| Cohort 2 Pre-Emptive Set | 0.6203 | 0.5813 | 0.6196 | 0.6223 |
| Cohort 6 Diagnostic Set | 0.7875 | 0.7799 | 0.7511 | 0.7601 |
| Cohort 6 Pre-Emptive Set | 0.7014 | 0.7073 | 0.655 | 0.6802 |

Notes
- Final Probabilities encoded as: P(patient having PH) = Sigmoid(k * z) = 1/(1+exp(-k * z))
- k is chosen based on mPAP ≥ 25 mmHg and TRV ≥ 3.4 m/s. P(patient with mPAP > 25mmHg having PH) > 0.88 for k = 2

FIG. 11C

| COHORT and SET | Probability Encoded Model Patient Wise AUC | Non Probability Encoded Model Patient Wise AUC | Probability Encoded Model Age Gender Wise AUC | Non Probability Encoded Model Age Gender Wise AUC |
|---|---|---|---|---|
| NON STRICT COHORTS | | | | |
| Cohort 2 Diagnostic Set | 0.7100 | 0.6960 | 0.6751 | 0.6615 |
| Cohort 2 PreEmptive Set | 0.6203 | 0.5813 | 0.6196 | 0.6220 |
| Cohort 6 Diagnostic Set | 0.7673 | 0.7799 | 0.7511 | 0.7501 |
| Cohort 6 PreEmptive Set | 0.7014 | 0.7073 | 0.6550 | 0.6662 |
| STRICT COHORTS | | | | |
| Cohort 1 Diagnostic Set | 0.7073 | 0.7068 | 0.6499 | 0.6650 |
| Cohort 1 PreEmptive Set | 0.6602 | 0.6349 | 0.6430 | 0.6412 |
| Cohort 5 Diagnostic Set | 0.8577 | 0.8839 | 0.8341 | 0.8638 |
| Cohort 5 PreEmptive Set | 0.7848 | 0.7861 | 0.7281 | 0.7603 |

FIG. 11D

| Model Description | Patient Wise AUC | | Age Gender Wise AUC | |
|---|---|---|---|---|
| | Cohort 3 | Cohort 5 | Cohort 3 | Cohort 5 |
| Optimal Model | 0.9076 | 0.8715 | 0.8947 | 0.8520 |
| Optimal Model - Residual Connections | 0.9023 | 0.8686 | 0.8918 | 0.8534 |
| Optimal Model - Residual + 1x1 Branch | 0.9021 | 0.8646 | 0.8907 | 0.8507 |
| Optimal Model - Residual + 1x1 + 1x3 Branch | 0.8992 | 0.8535 | 0.8881 | 0.8487 |

FIG. 11H

| Model Description | Patient Wise AUC | | Age Gender Wise AUC | |
|---|---|---|---|---|
| | Cohort 3 | Cohort 5 | Cohort 3 | Cohort 5 |
| New Model | 0.9076 | 0.8715 | 0.8547 | 0.8620 |
| New Model + Spectrogram | 0.9081 (+0.0005) | 0.8715 (+0.0000) | 0.8555 (+0.0008) | 0.8625 (+0.0005) |

FIG. 11I

|  | Diagnostic (1 month before or after diagnosis) | Pre-emptive (6–18 months before diagnosis) | ECGs from 18–36 months before diagnosis | ECGs from 36–60 months before diagnosis |
|---|---|---|---|---|
| PH Patients (N ECGs) | 4274 (11109) | 1206 (3661) | 1116 (3602) | 1001 (3515) |
| Control Patients (N ECGs) | 21931 (63659) | 21931 (63659) | 21931 (63659) | 21931 (63659) |
| AUC | 0.9436 (0.9392-0.9464) | 0.9023 (0.8952-0.9127) | 0.8728 (0.8589-0.8816) | 0.8466 (0.8318-0.8585) |
| Sensitivity | 0.8745 | 0.830 | 0.7956 | 0.7756 |
| Specificity | 0.8743 | 0.8308 | 0.7971 | 0.7764 |
| Diagnostic odds ratio | 47.5794 | 23.9908 | 14.8717 | 11.8336 |
| PPV | 0.5726 | 0.2119 | 0.1641 | 0.1366 |
| NPV | 0.9726 | 0.9889 | 0.9870 | 0.9868 |
| PPV (1% Prevalence) | 0.0657 | 0.0472 | 0.0381 | 0.0389 |
| NPV (1% Prevalence) | 0.9986 | 0.9979 | 0.9974 | 0.9971 |
| J Threshold | 0.0861 | 0.0528 | 0.040 | 0.0346 |

FIG. 11J

| Cohort / Set | Patient Wise AUC Mean-Sinus | Age Gender Wise AUC Mean-Sinus | Patient Wise AUC Mean (95% CI) - ALL | Age Gender Wise AUC Mean (95% CI) - ALL |
|---|---|---|---|---|
| COHORT 1: RHC ≥ 25 mmHg vs RHC <21 mmHg | 0.7501 | 0.7511 | 0.7613 (0.7527 <> 0.7695) | 0.7381 (0.7363 <> 0.7396) |
| COHORT 2: RHC ≥ 21 mmHg vs RHC <21 mmHg | 0.7352 | 0.7332 | 0.7502 (0.7442 <> 0.7583) | 0.7228 (0.7206 <> 0.725) |
| COHORT 3: RHC ≥ 25 mmHg vs RHC <21 mmHg + TRV ≤ 2.8 m/s | 0.9034 | 0.9 | 0.9059 (0.9047 <> 0.9069) | 0.8935 (0.8926 <> 0.8943) |
| COHORT 4: RHC ≥ 21 mmHg vs RHC <21 mmHg + TRV ≤ 2.8 m/s | 0.8887 | 0.8874 | 0.8927 (0.8913 <> 0.8944) | 0.8828 (0.882 <> 0.8836) |
| COHORT 5: TRV ≥ 3.4 m/s vs TRV ≤ 2.8 m/s | 0.8762 | 0.874 | 0.8701 (0.8688 <> 0.8716) | 0.8591 (0.8585 <> 0.8596) |
| COHORT 6: TRV ≥ 2.8 m/s vs TRV ≤ 2.8 m/s | 0.8236 | 0.8214 | 0.8193 (0.8183 <> 0.8212) | 0.813 (0.8112 <> 0.8147) |
| COHORT 8: RHC ≥ 25 mmHg vs RHC <21 mmHg + TRV ≤ 2.6 m/s | 0.9046 | 0.8967 | 0.9107 (0.9093 <> 0.912) | 0.8898 (0.889 <> 0.8905) |
| COHORT 9: RHC ≥ 21 mmHg vs RHC <21 mmHg + TRV ≤ 2.6 m/s | 0.8941 | 0.8867 | 0.8997 (0.8982 <> 0.901) | 0.8821 (0.8814 <> 0.8828) |
| COHORT 10: TRV ≥ 3.4 m/s vs TRV ≤ 2.6 m/s | 0.8906 | 0.8882 | 0.8847 (0.8831 <> 0.8867) | 0.8729 (0.8722 <> 0.8736) |
| COHORT 11: TRV ≥ 2.8 m/s vs TRV ≤ 2.6 m/s | 0.8433 | 0.8431 | 0.8389 (0.8375 <> 0.8402) | 0.8347 (0.8327 <> 0.8368) |

FIG. 11K

| Model Trained On | Model Evaluated On | Patient Wise AUC Cohort 3 | Patient Wise AUC Cohort 5 | Age Gender Wise AUC Cohort 3 | Age Gender Wise AUC Cohort 5 |
|---|---|---|---|---|---|
| Full Data | Full Data | 0.9059 | 0.8701 | 0.8935 | 0.8591 |
| Full Data | On Patients who never had "pacemakers" | 0.9016 | 0.8633 | 0.9005 | 0.8581 |
| Full Data | On ECGs without "pacemakers" | 0.9021 | 0.8677 | 0.8993 | 0.8619 |
| On Patients who never had "pacemakers" | On Patients who never had "pacemakers" | 0.8853 | 0.8632 | 0.8924 | 0.8583 |
| On ECGs without "pacemakers" | On ECGs without "pacemakers" | 0.9018 | 0.8683 | 0.8958 | 0.8632 |

FIG. 11L

| | Pre-capillary PH | Isolated Post-Capillary PH | Combined Pre- and Post-Capillary PH |
|---|---|---|---|
| PH Patients (N ECGs) | 1133 (2025) | 1745 (4965) | 1572 (4151) |
| Control Patients (N ECGs) | 28401 (82635) | 28401 (82635) | 28401 (82635) |
| AUC | 0.9464 | 0.9378 | 0.9727 |
| Sensitivity | 0.9743 | 0.8657 | 0.9220 |
| Specificity | 0.8743 | 0.8661 | 0.9218 |
| Diagnostic odds ratio | 46.2633 | 40.4373 | 147.61030 |
| PPV | 0.2142 | 0.2830 | 0.3936 |
| NPV | 0.9941 | 0.9803 | 0.9956 |
| PPV (1% Prevalence) | 0.0656 | 0.0613 | 0.1064 |
| NPV (1% Prevalence) | 0.9985 | 0.9984 | 0.9991 |
| J Threshold | 0.0875 | 0.0789 | 0.1713 |

FIG. 11N

| Cohort / Set | Patient Wise AUC Mean (95% CI) | Age Gender Wise AUC Mean (95% CI) |
|---|---|---|
| COHORT 3: RHC ≥ 25 mmHg vs RHC < 21 mmHg + TRV < 2.8 m/s | 0.9059 (0.9047 <-> 0.9069) | 0.8935 (0.8926 <-> 0.8943) |
| COHORT 5: TRV > 3.4 m/s vs TRV < 2.8 m/s | 0.8701 (0.8688 <-> 0.8716) | 0.8591 (0.8585 <-> 0.8596) |

FIG. 11O

| Model Trained On | Model Evaluated On | Patient Wise AUC | | Age Gender Wise AUC | |
|---|---|---|---|---|---|
| | | Cohort 3 | Cohort 5 | Cohort 3 | Cohort 5 |
| Full Set | Full Set | 0.9146 (0.9058 <> 0.9188) | 0.8955 (0.8897 <> 0.8998) | 0.9205 (0.8988 <> 0.9058) | 0.8883 (0.8859 <> 0.8927) |
| Full Set | HF Patients Removed | 0.9204 (0.915 <> 0.925) | 0.8907 (0.8832 <> 0.904) | 0.923 (0.9146 <> 0.9257) | 0.9024 (0.8989 <> 0.8962) |
| HF Patients Removed | HF Patients Removed | 0.9201 (0.9147 <> 0.9247) | 0.897 (0.8819 <> 0.9026) | 0.9234 (0.9135 <> 0.9258) | 0.8978 (0.8941 <> 0.9012) |

FIG. 11R

|  | Reference* | Remove Heart Transplant Patients | Remove Liver Transplant Patients | Remove Heart and Liver Transplant Patients |
|---|---|---|---|---|
| Disease Criteria | 0-6 mo. before diagnosis | 0-6 mo. before diagnosis | 0-6 mo. before diagnosis | 0-6 mo. before diagnosis |
| Control Criteria | Across all patient history | Across all patient history | Across all patient history | Across all patient history |
| Disease Patients | 4657 | 4611 | 4627 | 4590 |
| Control Patients | 23787 | 23770 | 23589 | 23573 |
| AUC | 0.9115 +- 0.0007 | 0.9111 +- 0.0007 | 0.9111 +- 0.0007 | 0.9109 +- 0.0007 |
| Sensitivity | 0.8332 +- 0.0015 | 0.832 +- 0.0018 | 0.8327 +- 0.0016 | 0.8321 +- 0.0015 |
| Specificity | 0.833 +- 0.0014 | 0.8334 +- 0.0013 | 0.8326 +- 0.0014 | 0.8333 +- 0.0011 |
| Odds Ratio | 24.9331 22.9195 <-> 27.1236 | 24.6447 22.6487 <-> 26.8166 | 24.3703 22.3994 <-> 26.5146 | 24.6439 22.6453 <-> 26.8188 |
| Prevalence | 0.163725 | 0.162466 | 0.163985 | 0.16298 |
| PPV | 0.494600 | 0.4903 | 0.4908 | 0.4921 |
| NPV | 0.962200 | 0.9624 | 0.962 | 0.9622 |
| PPV (1:1) | 0.833033 | 0.833166 | 0.832617 | 0.8331 |
| NPV (1:1) | 0.833167 | 0.832235 | 0.832683 | 0.832301 |
| Threshold | 0.1936 | 0.1936 | 0.1936 | 0.1936 |

FIG. 11S

| | Reference* | Remove Heart Surgery Patients | Remove ECGs after Heart Surgery |
|---|---|---|---|
| Disease Criteria | 0-6 mo. before diagnosis | 0-6 mo. before diagnosis | 0-6 mo. before diagnosis |
| Control Criteria | Across all patient history | Across all patient history | Across all patient history |
| Disease Patients | 4607 | 4611 | 4560 |
| Control Patients | 23787 | 23351 | 23747 |
| AUC | 0.9015 +/- 0.0007 | 0.9014 +/- 0.0007 | 0.9013 +/- 0.0006 |
| Sensitivity | 0.8332 +/- 0.0015 | 0.8295 +/- 0.002 | 0.8308 +/- 0.0018 |
| Specificity | 0.833 +/- 0.0014 | 0.837 +/- 0.0011 | 0.8342 +/- 0.0012 |
| OddsRatio | 24.9931 22.9195 <-> 27.1236 | 25.0153 22.9356 <-> 27.2809 | 24.1978 22.2415 <-> 26.3352 |
| Prevalence | 0.162225 | 0.163846 | 0.161603 |
| PPV | 0.494000 | 0.4847 | 0.4897 |
| NPV | 0.962260 | 0.9638 | 0.9635 |
| PPV (1.1) | 0.833030 | 0.835788 | 0.833634 |
| NPV (1.1) | 0.833167 | 0.832269 | 0.831371 |
| Threshold | 0.1936 | 0.1936 | 0.1936 |

FIG. 11T

| Performance parameter | Data set | | |
|---|---|---|---|
| | Diagnostic (1 month before or after diagnosis) | Pre-emptive (6-18 months before diagnosis) | ECGs from 36-60 months before diagnosis |
| N Patients | 22191 | 19469 | 19249 |
| N ECGs | 93290 | 88604 | 86688 |
| AUC | 0.9287 | 0.8920 | 0.8230 |
| Sensitivity, % | 85.50 | 80.81 | 74.59 |
| Specificity, % | 85.49 | 80.58 | 74.60 |
| Diagnostic odds ratio | 33.0604 | 17.3212 | 9.24150 |
| PPV | 0.5460 | 0.2027 | 0.1248 |
| NPV | 0.9846 | 0.9859 | 0.9848 |

FIG. 11U

|  | 0-6 | 6-12 | 12-18 | 18-24 | 24-30 | 30-36 | 36-42 | 42-48 | 48-54 | 54-60 |
|---|---|---|---|---|---|---|---|---|---|---|
| PH Patients (N ECGs) | 4477 (9960) | 945 (1930) | 729 (1731) | 619 (1277) | 583 (1198) | 532 (1127) | 482 (923) | 441 (887) | 428 (862) | 409 (843) |
| Control Patients (N ECGs) | 21931 (63659) | 21931 (63659) | 21931 (63659) | 21931 (63659) | 21931 (63659) | 21931 (63659) | 21931 (63659) | 21931 (63659) | 21931 (63659) | 21931 (63659) |
| AUC | 0.9407 | 0.9084 | 0.8971 | 0.8908 | 0.8791 | 0.8796 | 0.8712 | 0.8712 | 0.8483 | 0.8589 |
| Sensitivity | 0.8685 | 0.8343 | 0.830 | 0.8134 | 0.8054 | 0.8048 | 0.7961 | 0.8027 | 0.7817 | 0.7891 |
| Specificity | 0.8685 | 0.8343 | 0.8308 | 0.8137 | 0.8080 | 0.8061 | 0.7961 | 0.8052 | 0.7788 | 0.7902 |
| Diagnostic odds ratio | 43.5592 | 24.1589 | 26.3193 | 19.6154 | 17.0997 | 17.5793 | 14.9814 | 17.0485 | 11.9541 | 13.9714 |
| PPV | 0.5736 | 0.1601 | 0.1441 | 0.1104 | 0.0999 | 0.0920 | 0.0784 | 0.0767 | 0.0641 | 0.0655 |
| NPV | 0.970 | 0.9922 | 0.9936 | 0.9937 | 0.9936 | 0.9943 | 0.9944 | 0.9952 | 0.9943 | 0.9950 |
| PPV (1% Prevalence) | 0.0625 | 0.0485 | 0.0472 | 0.0422 | 0.0406 | 0.0402 | 0.0379 | 0.040 | 0.0345 | 0.0366 |
| NPV (1% Prevalence) | 0.9985 | 0.9980 | 0.9979 | 0.9977 | 0.9976 | 0.9976 | 0.9974 | 0.9975 | 0.9972 | 0.9973 |
| J Threshold | 0.0802 | 0.0547 | 0.0528 | 0.0460 | 0.0437 | 0.0432 | 0.0397 | 0.0430 | 0.0352 | 0.0380 |

FIG. 11V

| | Reference for Aggregate: Any ECS Score | Min ECG Score | Max ECG Score | Mean ECG Score |
|---|---|---|---|---|
| Disease Criteria | ≥ 2 ECGs 0-6 mo. before diagnosis date, >7 days btwn ECGs | ≥ 2 ECGs 0-6 mo. before diagnosis date, >7 days btwn ECGs | ≥ 2 ECGs 0-6 mo. before diagnosis date, >7 days btwn ECGs | ≥ 2 ECGs 0-6 mo. before diagnosis date, >7 days btwn ECGs |
| Control Criteria | ECGs within 6 mo. windows with ≥ 2 ECGs, > 7 days btwn ECGs | ECGs within 6 mo. windows with ≥ 2 ECGs, > 7 days btwn ECGs | ECGs within 6 mo. windows with ≥ 2 ECGs, > 7 days btwn ECGs | ECGs within 6 mo. windows with ≥ 2 ECGs, > 7 days btwn ECGs |
| Disease Patients | 4142 | 4142 | 4142 | 4142 |
| Control Patients | 6993 | 6993 | 6993 | 6993 |
| AUC | 0.896 +- 0.001 | 0.9336 +- 0.0005 | 0.8563 +- 0.0007 | 0.8955 +- 0.0006 |
| Sensitivity | 0.8137 +- 0.0013 | 0.857 +- 0.0009 | 0.7772 +- 0.0012 | 0.811 +- 0.0011 |
| Specificity | 0.8135 +- 0.0028 | 0.8575 +- 0.0014 | 0.7779 +- 0.0017 | 0.8111 +- 0.0016 |
| OddsRatio | 19.7718 17.905 <-> 21.8332 | 36.5506 32.7387 <-> 40.8062 | 12.4401 11.3393 <-> 13.6478 | 18.6419 16.8952 <-> 20.5693 |
| Prevalence | 0.371980 | 0.371980 | 0.371980 | 0.371980 |
| PPV | 0.726100 | 0.781500 | 0.675900 | 0.718300 |
| NPV | 0.881800 | 0.910980 | 0.856400 | 0.879700 |
| PPV (1:1) | 0.813537 | 0.857429 | 0.777744 | 0.811081 |
| NPV (1:1) | 0.813663 | 0.857071 | 0.777356 | 0.811019 |
| Threshold | 0.2127 | 0.1538 | 0.2712 | 0.2173 |

FIG. 12A

| | Reference for Aggregate: Any ECS Score | Min ECG Score | Max ECG Score | Mean ECG Score |
|---|---|---|---|---|
| Disease Criteria | ≥ 2 ECGs 0-6 mo. before diagnosis date, >7 days btwn ECGs | ≥ 2 ECGs 0-6 mo. before diagnosis date, >7 days btwn ECGs | ≥ 2 ECGs 0-6 mo. before diagnosis date, >7 days btwn ECGs | ≥ 2 ECGs 0-6 mo. before diagnosis date, >7 days btwn ECGs |
| Control Criteria | Randomly selected 6 mo. windows with ≥ 2 ECGs, > 7 days btwn ECGs | Randomly selected 6 mo. windows with ≥ 2 ECGs, > 7 days btwn ECGs | Randomly selected 6 mo. windows with ≥ 2 ECGs, > 7 days btwn ECGs | Randomly selected 6 mo. windows with ≥ 2 ECGs, > 7 days btwn ECGs |
| Disease Patients | 4142 | 4142 | 4142 | 4142 |
| Control Patients | 6993 | 6993 | 6993 | 6993 |
| AUC | 0.895 +- 0.0009 | 0.9337 +- 0.0003 | 0.8563 +- 0.0005 | 0.8956 +- 0.0005 |
| Sensitivity | 0.8133 +- 0.001 | 0.8573 +- 0.0011 | 0.7782 +- 0.0015 | 0.8107 +- 0.0011 |
| Specificity | 0.8131 +- 0.0020 | 0.8574 +- 0.0 | 0.7781 +- 0.0 | 0.8105 +- 0.0 |
| OddsRatio | 19.048 17.2568 <-> 21.0252 | 36.7135 32.8799 <-> 40.9941 | 12.3815 11.2865 <-> 13.5828 | 18.4673 16.7394 <-> 20.3736 |
| Prevalence | 0.371980 | 0.371980 | 0.371980 | 0.371980 |
| PPV | 0.719800 | 0.781200 | 0.675300 | 0.717400 |
| NPV | 0.881100 | 0.911400 | 0.856200 | 0.879200 |
| PPV (1:1) | 0.813137 | 0.857366 | 0.778122 | 0.810538 |
| NPV (1:1) | 0.813263 | 0.857314 | 0.778178 | 0.810662 |
| Threshold | 0.2132 | 0.1538 | 0.2705 | 0.2177 |

FIG. 12B

| | Reference* | Remove Challenge mPAP |
|---|---|---|
| Disease Criteria | 0-6 mo. before diagnosis | 0-6 mo. before diagnosis |
| Control Criteria | Across all patient history | Across all patient history |
| Disease Patients | 4657 | 4336 |
| Control Patients | 23787 | 23787 |
| AUC | 0.9115 +/- 0.0007 | 0.9256 +/- 0.0007 |
| Sensitivity | 0.8332 +/- 0.0015 | 0.8654 +/- 0.0016 |
| Specificity | 0.833 +/- 0.0014 | 0.8332 +/- 0.0014 |
| OddsRatio | 24.9331 22.9395 <-> 27.1236 | 31.7795 28.9376 <-> 34.9804 |
| Prevalence | 0.163725 | 0.153578 |
| PPV | 0.494600 | 0.4834 |
| NPV | 0.962200 | 0.9714 |
| PPV (1:1) | 0.835093 | 0.838403 |
| NPV (1:1) | 0.833167 | 0.860922 |
| Threshold | 0.1936 | 0.1936 |

FIG. 12C

| | Reference for Aggregate: Any ECS Score | Min ECG Score | Max ECG Score | Mean ECG Score |
|---|---|---|---|---|
| Disease Criteria | ≥ 2 ECGs 0-6 mo. before diagnosis date, >7 days btwn ECGs, drop challenge induced PH pts | ≥ 2 ECGs 0-6 mo. before diagnosis date, >7 days btwn ECGs, drop challenge induced PH pts | ≥ 2 ECGs 0-6 mo. before diagnosis date, >7 days btwn ECGs, drop challenge induced PH pts | ≥ 2 ECGs 0-6 mo. before diagnosis date, >7 days btwn ECGs, drop challenge induced PH pts |
| Control Criteria | ECGs within 6 mo. windows with ≥ 2 ECGs, > 7 days btwn ECGs | ECGs within 6 mo. windows with ≥ 2 ECGs, > 7 days btwn ECGs | ECGs within 6 mo. windows with ≥ 2 ECGs, > 7 days btwn ECGs | ECGs within 6 mo. windows with ≥ 2 ECGs, > 7 days btwn ECGs |
| Disease Patients | 3813 | 3813 | 3813 | 3813 |
| Control Patients | 6993 | 6993 | 6993 | 6993 |
| AUC | 0.9127 +- 0.0009 | 0.9461 +- 0.0005 | 0.8778 +- 0.0007 | 0.914 +- 0.0006 |
| Sensitivity | 0.8313 +- 0.0013 | 0.872 +- 0.0013 | 0.796 +- 0.0016 | 0.8319 +- 0.0013 |
| Specificity | 0.8313 +- 0.0025 | 0.8722 +- 0.0012 | 0.7961 +- 0.0016 | 0.8319 +- 0.0013 |
| OddsRatio | 24.4516 22.005 <-> 27.1758 | 46.7435 41.5267 <-> 52.6150 | 15.2855 13.8594 <-> 16.8583 | 24.5194 22.063 <-> 27.2494 |
| Prevalence | 0.352860 | 0.352860 | 0.352860 | 0.352860 |
| PPV | 0.727600 | 0.787700 | 0.681200 | 0.729300 |
| NPV | 0.901500 | 0.926400 | 0.877400 | 0.901000 |
| PPV (1:1) | 0.831300 | 0.872174 | 0.796060 | 0.831900 |
| NPV (1:1) | 0.831300 | 0.872026 | 0.796020 | 0.831900 |
| Threshold | 0.2438 | 0.1742 | 0.2973 | 0.2429 |

FIG. 12D

| Metric / Threshold | Measure |
|---|---|
| AUC | 0.8664 |
| Sensitivity | 0.7699 |
| Specificity | 0.8091 |
| Odds Ratio | 14.0457 |
| PPV | 0.8391 |
| NPV | 0.7311 |
| J Threshold | 0.3618 |

SYSTEMS AND METHODS FOR DIAGNOSING A HEALTH CONDITION BASED ON PATIENT TIME SERIES DATA

CROSS-REFERENCE TO RELATED APPLICATIONS

This application is a continuation of U.S. patent application Ser. No. 17/552,246, filed on Dec. 15, 2021, entitled "Systems and Methods for Diagnosing a Health Condition Based on Patient Time Series Data," which claims priority under 35 U.S.C. § 119(e) to U.S. Provisional Application No. 63/156,531, entitled "Systems and Methods for Diagnosing a Health Condition Based on Patient Time Series Data," filed Mar. 4, 2021, and to U.S. Provisional Application No. 63/126,331, entitled "Systems and Methods for Diagnosing a Health Condition Based on Patient Time Series Data," filed Dec. 16, 2020, each of which is incorporated by reference herein in its entirety.

FIELD OF THE INVENTION

This application relates generally to digital analysis of patient time series data and specifically to techniques for diagnosing a health condition based on patient time series data.

BACKGROUND

Timely and accurate diagnosis of health conditions is an important aspect of healthcare. On one hand, the early diagnosis of health conditions can often improve patient outcomes. For example, interventions are often more effective when a health condition is at a less advanced stage of progression. On the other hand, diagnostic tests can be costly, time-intensive, risky, or burdensome. As a result, diagnosis of many health conditions is challenging, particularly at an early stage of the condition, e.g., before a patient is exhibiting overt symptoms or has undergone extensive testing.

Accordingly, it is desirable to develop improved diagnostic techniques that address one or more of these challenges.

SUMMARY OF THE DISCLOSURE

In an aspect, a method for diagnosing a health condition based on patient time series data is disclosed. The method includes receiving, using one or more hardware processors, patient time series data, wherein the patient time series data includes an electrocardiogram (ECG) waveform, identifying, using the one or more hardware processors, a training set of health records, wherein the training set of health records includes health records of patients who have been diagnosed with a health condition of interest and a control group of patients who have not been diagnosed with the condition and identifying the training set of health records includes identifying one or more cohorts of the patients, training, using the one or more hardware processors, a plurality of neural network models for each cohort of the patients using the training set of health records, selecting, using the one or more hardware processors, one or more highest performing models from the plurality of trained neural network models, executing, using the one or more hardware processors, the one or more highest performing models to diagnose a health condition as a function of the patient time series data, wherein executing the one or more highest performing models includes preprocessing the time series data, wherein preprocessing the time series data includes extracting one or more discrete metrics as a function of the time series data, wherein the one or more discrete metrics includes a QT interval of an ECG waveform and aggregating, using the one or more hardware processors, a plurality of outputs of the one or more highest performing models to generate an aggregate diagnosis of the health condition.

In another aspect, a system for diagnosing a health condition based on patient time series data is disclosed. The system includes a non-transitory memory and one or more hardware processors configured to read instructions from the non-transitory that, when executed, cause the one or more hardware processors to perform operations including receive patient time series data, wherein the patient time series data includes an electrocardiogram (ECG) waveform, identify a training set of health records, wherein the training set of health records includes health records of patients who have been diagnosed with a health condition of interest and a control group of patients who have not been diagnosed with the condition and identifying the training set of health records includes identifying one or more cohorts of the patients, train a plurality of neural network models for each cohort of the patients using the training set of health records, select one or more highest performing models from the plurality of trained neural network models, execute the one or more highest performing models to diagnose a health condition as a function of the patient time series data, wherein executing the one or more highest performing models includes preprocessing the time series data, wherein preprocessing the time series data includes extracting one or more discrete metrics as a function of the time series data, wherein the one or more discrete metrics includes a QT interval of an ECG waveform and aggregate a plurality of outputs of the one or more highest performing models to generate an aggregate diagnosis of the health condition.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 10A-10H are simplified diagrams showing preliminary experimental data associated with the techniques of FIGS. 1-9 when applied to the diagnosis of pulmonary hypertension according to some embodiments;

FIGS. 11A-11V and FIGS. 12A-12D are simplified diagrams summarizing the structure and performance of preliminary neural network models according to some embodiments;

DETAILED DESCRIPTION

Figure 1:
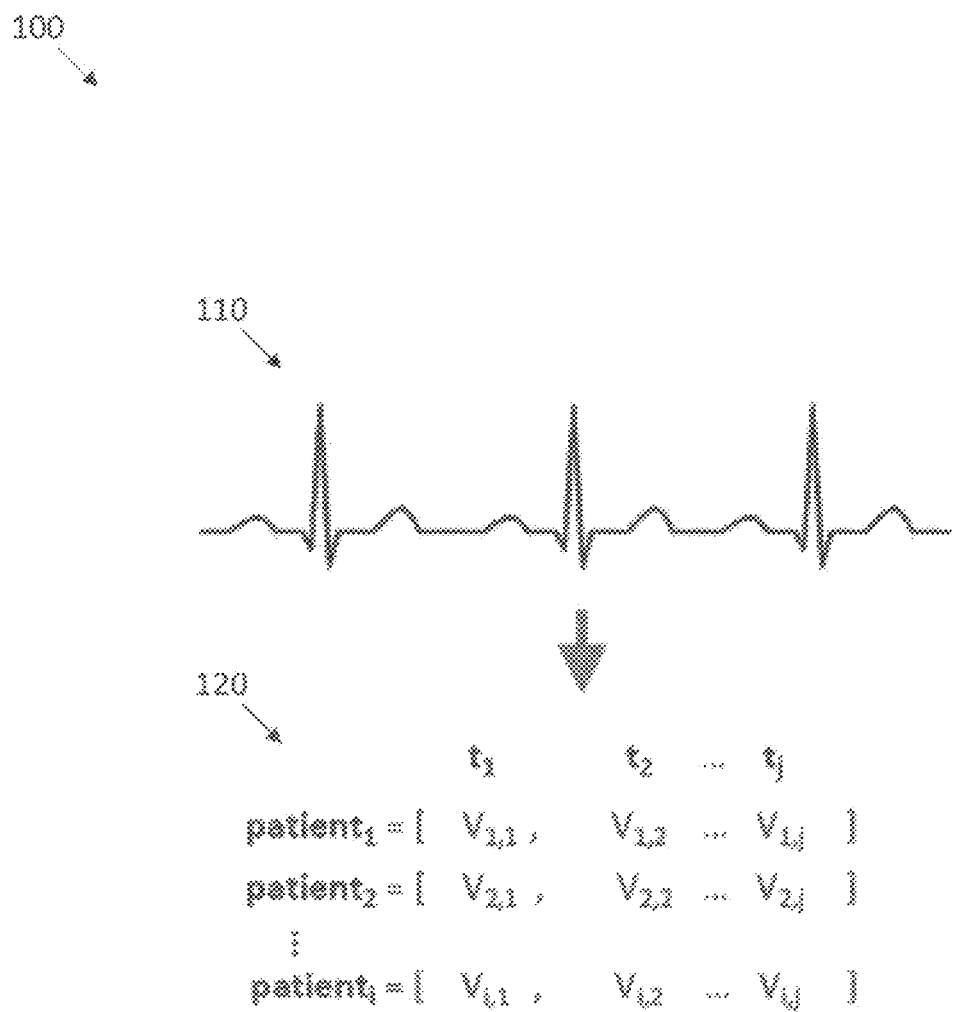
FIG. 1 is a simplified diagram of an ECG waveform according to some embodiments.

Patient data is captured and stored in a variety of ways. For example, patient data can include discrete data points, such as patient age, gender, health conditions, and the like. The patient data can be stored in structured, unstructured, or semi-structured formats. For example, patient data may be contained in physician's notes in an unstructured form, a structured database, an electronic health record that includes a combination of structured and unstructured data, or the like.

Patient data can be used to diagnose one or more health conditions of the patient. For example, a physician or other trained individual can analyze the available patient data to diagnose a patient for a given condition. Based on the diagnosis, a treatment plan or other form of intervention may be recommended.

Some patient data can include time series data. In general, time series data captures to one or more patient characteristics or measurements as a function of time. One example of time series data is electrocardiogram (ECG or EKG) data, which measures electrical activity associated with the heart as a function of time. ECG data can be represented as a waveform in the time domain, e.g., voltage as a function of time. Additionally or alternatively, ECG data can be converted to the frequency domain. For example, a spectrogram can be computed from the ECG waveform using a short time Fourier Transform (STFT).

In some cases, discrete metrics can be derived from time series data. These discrete metrics can be analyzed individually or can be themselves be utilized as time series data, e.g., discrete metrics taken over multiple visits can be used to analyze symptoms over time. For example, based on an ECG waveform, a QT interval can be derived. The QT interval reflects the amount of time between characteristic points of the ECG waveform. However, the QT interval (like other discrete metrics derived from time series data) generally does not comprehensively capture the information contained in the ECG waveform.

Nevertheless, metrics derived from time series data, rather than the underlying time series data itself, are frequently used in the diagnosis of patient conditions. For example, the discrete metrics may be easier for physicians to compare and interpret than the underlying time series data. In some situations, the underlying time series data is discarded after the discrete metrics are derived. In these cases, future diagnoses are based on the derived metrics and not on the raw time series data.

Although discrete metrics derived from time series may be adequate for diagnosing certain patient conditions, these metrics generally do not capture the complete information of the underlying time series data. Consequently, they may not be conducive to identifying patterns in the time series data that could otherwise be used to improve the timeliness and accuracy of the diagnosis or which may be used to diagnose other patient conditions. For example, whereas the QT interval may be an effective tool for diagnosing certain conditions directly associated with the heart (e.g., left ventricular dysfunction, atrial fibrillation, or the like), it may be difficult to diagnose conditions with a more attenuated connection to the heart (e.g., pulmonary hypertension) based on the QT interval. Likewise, it may be difficult to segment a patient population into patient subgroups based on the discrete metrics. Furthermore, a given discrete metric (e.g., QT interval) may be helpful to diagnose a disease at a certain point in time (e.g., at a later stage of development of the disease), but other features may exist in the underlying time series data which would allow for more timely diagnosis at an earlier stage of development.

In addition, because the underlying time series data is often discarded after computing the discrete metrics, it may be difficult to ascertain additional metrics associated with the time series data that are correlated with a particular diagnosis. For example, whereas the QT interval measures a particular interval of an ECG waveform, there may be other intervals that are more strongly correlated with a particular diagnosis than the QT interval. However, if this interval is not captured in an existing metric, it may be difficult to discover this correlation.

Accordingly, it is desirable to develop improved diagnostic techniques that use patient time series data, such as ECG waveforms and spectrograms, for the diagnosis and classification of patients.

FIG. 1 is a simplified diagram of an ECG waveform 100 according to some embodiments. In some embodiments, ECG waveform 100 may be measured using a commercial ECG monitor or by another suitable device. ECG waveform 100 includes time series data that represents the ECG level (e.g., a voltage level) as a function of time. Although ECG waveform 100 corresponds to a continuous-time analog signal, for digital processing purposes it is converted to a digital representation that includes a series of samples at discrete intervals. Accordingly, ECG waveform 100 may be represented as a signal trace 110. Additionally or alternatively, ECG waveform 120 may be represented using a vector representation 120. In the vector representation, each element corresponds to an ECG level for a given sample. For example, the element V1,1 corresponds to an ECG level (e.g., voltage) for a particular patient (patient1) at a particular sampling time ti. It is to be understood that ECG waveform 100 is illustrative and that ECG waveforms may generally have features other than those depicted in FIG. 1. Moreover, ECG waveform 100 may correspond to raw ECG measurement data (e.g., voltage signals) or processed data (e.g., data that has been scaled, filtered, normalized, compressed, etc.).

Figure 2:
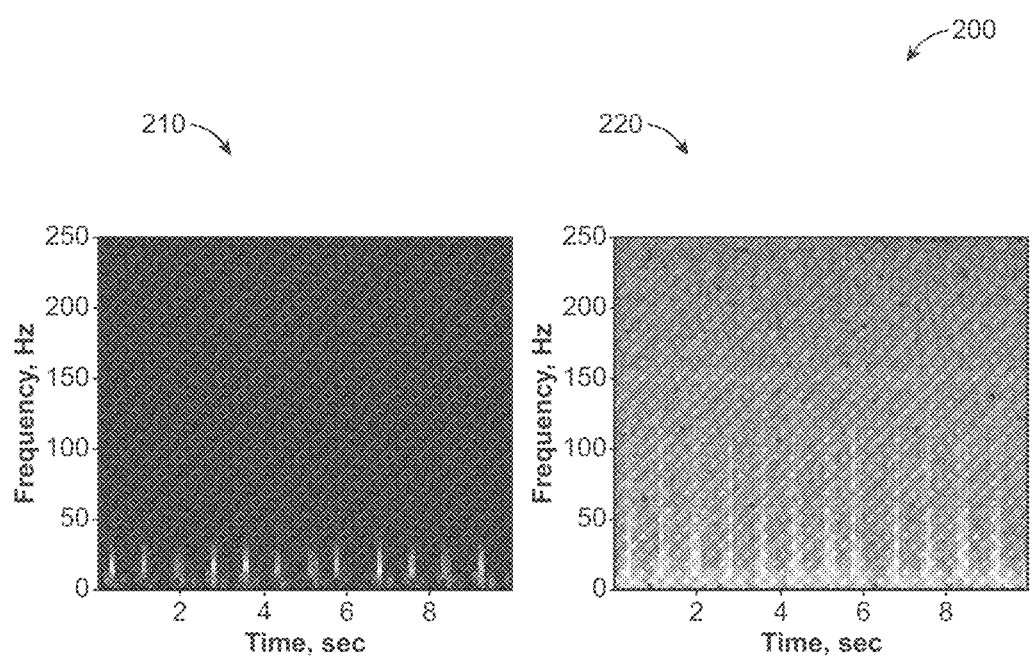
FIG. 2 is a simplified diagram of an ECG spectrogram according to some embodiments.

FIG. 2 is a simplified diagram of an ECG spectrogram 200 according to some embodiments. In some embodiments, ECG spectrogram 200 may be computed based on an ECG waveform, such as ECG waveform 100. Whereas the representations 110 and 120 of ECG waveform 100 shown in FIG. 1 are time-domain representations of an ECG waveform, ECG spectrogram 200 is a frequency-domain representation that depicts the frequency spectrum of the ECG waveform at a given point in time. The frequency spectrum may be determined as a function of time. In some embodiments, ECG spectrogram 200 may be computed using a short time Fourier Transform (STFT). For example, the STFT may be configured to calculate the frequency spectrum based on a plurality of samples of the ECG waveform (e.g., 128 samples) and may split the frequency spectrum into a plurality of frequency bins (e.g., 400 bins). The results can be plotted using a linear scale 210, a logarithmic scale 220, or the like.

Figure 3:
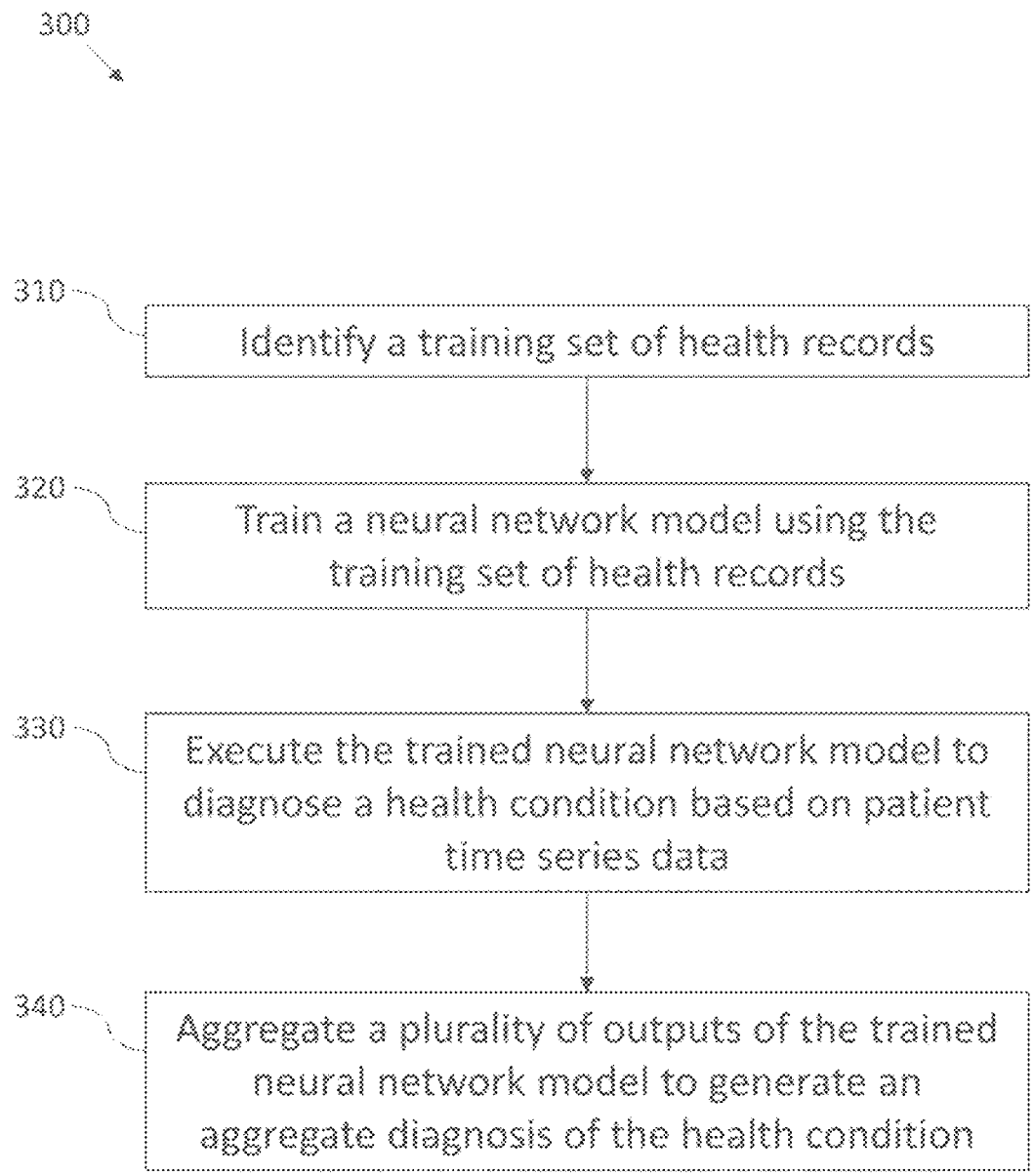
FIG. 3 is a simplified diagram of a method for patient classification based on patient time series data according to some embodiments.

FIG. 3 is a simplified diagram of a method 300 for diagnosis of a health condition based on patient time series data according to some embodiments. In some embodiments, the patient time series data may include an ECG waveform, such as ECG waveform 100, an ECG spectrogram, such as ECG spectrogram 200, or both.

One example of a health condition that may be diagnosed using method 300 is pulmonary hypertension. Pulmonary hypertension is a particularly strong candidate for early diagnosis using ECG data for several reasons. First, pulmonary hypertension has no known cure, but early intervention can result in longer life expectancy. In this regard, a delay in treatment directly impacts the expected outcome. Second, pulmonary hypertension is commonly misdiagnosed, e.g., as asthma. Existing diagnostic techniques lack sufficient precision to reliably distinguish these conditions, which in turn may result in additional delays in proper treatment. Third, pulmonary hypertension is diagnosed using invasive methods, such as right heart catheterization measurements. Other methods, such as echocardiograms may be used, but accurate diagnosis using this technique is more unreliable than invasive testing.

Method 300 may address these challenges by providing an accessible, non-invasive diagnostic tool for identifying patients as being at risk for pulmonary hypertension. Because ECG measurements are readily obtainable, the likelihood that diagnostic data exists to enable early detection of pulmonary hypertension using method 300 increases. To the extent method 300 does not provide a conclusive diagnosis, it may at least be used to classify patients who are at risk, and who may subsequently undergo more extensive testing, including invasive testing.

At a process 310, a training set of health records is identified. The training set of health records may include health records of patients who have been diagnosed with a health condition of interest (e.g., pulmonary hypertension), as well as a control group of patients who have not been diagnosed with the condition. The training set of health records may include a variety of structured, unstructured, and semi-structured health data. For example, a given health record may include a patient's age, sex, ethnicity, date of diagnosis, treatment information (e.g., inpatient and outpatient medications and procedures), or the like. In some embodiments, the health record may include measurements and other information associated with the diagnosis. For example, when the health condition is pulmonary hypertension, the diagnosis information may include mean pulmonary arterial pressure (mPAP) or pulmonary vascular resistance (PVR) measurements associated with a right heart catheterization procedure, tricuspid regurgitation velocity (TRV) measurements associated with an echocardiogram, ICD codes denoting the specific conditions that the patient was diagnosed for, or the like.

The training set of health records includes at least one set of time series data for each patient. For example, the time series data may include ECG data, such as ECG waveform data, ECG spectrogram data, or both. The set of time series data is measured at a time prior to a positive diagnosis for the condition of interest. That is, the time series data reflects the condition of the patient prior to being diagnosed for the condition. In this regard, the time series data may include patterns or other early indicators suggesting that the patient has (or is at risk of having) the condition in advance of a formal diagnosis. In some instances, these patterns or early indicators may not be readily detectable using discrete metrics derived from the time series data, such as QT intervals in the case of ECG data. Nevertheless, the training set of health records may, in some embodiments, include discrete metrics derived from the time series data, in addition to the time series data itself.

In some embodiments, a plurality of sets of time series data may be provided for one or more of the patients. For patients who were eventually diagnosed with the condition of interest, the sets of time series data may include one or more diagnostic sets, which are sets captured close to the date of the positive diagnosis (e.g., within one month before and after the date of the positive diagnosis). Moreover, the sets of time series data may include one or more preemptive sets, which are sets captured significantly earlier than the date of the positive diagnosis (e.g., six to 18 months prior to the date of the positive diagnosis). For patients in the control group (i.e., patients who did not test positive for the condition of interest), the sets may include any or all of the sets of time series data captured for that patient.

In some embodiments, identifying the training set of health records may include identifying one or more cohorts of patients. For example, the one or more cohorts may be identified based on one or more of structured, unstructured, or semi-structured data associated with the time series data. Examples of cohorts include patients who were diagnosed using a particular testing method and whose test results were in a particular range. In the case of pulmonary hypertension, for example, patients diagnosed using right heart catheterization, echocardiogram, or clinical notes (e.g., a physician's diagnosis) may be assigned to different cohorts.

Table 1 below illustrates examples of cohorts in the context of pulmonary hypertension diagnosis. The left column lists the cohort sizes for patients who were diagnosed with pulmonary hypertension, and the right column lists the size of the control groups who did not test positive. In certain cohorts, one of more of the cohorts was supplemented with patients from other cohorts. For example, in cohort 3, the negative set of patients identified as negative based on right heart catheterization (mPAP measurement) was supplemented with patients identified as negative based on echocardiogram results (TRV measurements). Cohort 3 has been selected for its clinical functionality, and the performance metrics disclosed herein are based on the patients in Cohort 3 unless otherwise specified.

TABLE 1

| Positive Cohort | Positive | Unique Patients |
|---|---|---|
| 1 | mPAP ≥ 25 mmHg | 11215 |
| 2 | mPAP ≥ 21 mmHg | 12827 |
| 3 | mPAP > 25 mmHg | 11215 |
| 4 | mPAP ≥ 21 mmHg | 12827 |
| 5 | TRV ≥ 3.4 m/s | 15515 |
| 6 | TRV > 2.8 m/s | 39238 |
| 7 | Echo + Clinical Notes Positive | 5994 |
| 8 | mPAP ≥ 25 mmHg | 11215 |
| 9 | mPAP ≥ 21 mmHg | 12827 |
| 10 | TRV ≥ 3.4 m/s | 15515 |
| 11 | TRV > 2.8 m/s | 39238 |
| 12 | mPAP >20 mmHg + TRV > 3.4 m/s | 19422 |

| Negative Cohort | Negative | Unique Patients |
|---|---|---|
| 1 | mPAP < 21 mmHg | 2293 |
| 2 | mPAP < 21 mmHg | 2293 |
| 3 | mPAP < 21 mmHg + TRV < 2.8 m/s | 50768 |
| 4 | mPAP < 21 mmHg + TRV < 2.8 m/s | 50768 |
| 5 | TRV < 2.8 m/s | 49614 |
| 6 | TRV < 2.8 m/s | 49614 |
| 7 | Echo + Clinical Notes Negative | 56835 |
| 8 | mPAP < 21 mmHg + TRV < 2.6 m/s | 41804 |
| 9 | mPAP < 21 mmHg + TRV < 2.6 m/s | 41804 |
| 10 | TRV < 2.6 m/s | 40263 |
| 11 | TRV < 2.6 m/s | 40263 |
| 12 | mPAP < 20 mmHg + TRV < 2.8 m/s | 42144 |

In some embodiments, a diagnosis may be provided in a binary manner (e.g., "positive" and "negative") or may be probability encoded to reflect uncertainty in the diagnosis. For example, in cohorts where the difference between a positive and negative diagnosis is relatively large (e.g., Cohort 1 has a 4 mmHg difference between a positive diagnosis (mPAP≥25 mmHg) and a negative diagnosis (mPAP<21 mmHg)), the diagnosis may be provided in a binary manner. Conversely, in cohorts where the difference between a positive and negative diagnosis is relatively small (e.g., Cohort 2 abruptly transitions between a positive diagnosis (mPAP≥21 mmHg) and a negative diagnosis (mPAP<21 mmHg)), the diagnosis may be provided in a probability encoded manner that reflects the possibility that some members of the cohort may be misdiagnosed, particularly those near the transition point.

In some embodiments, the training set of health records for each cohort may be obtained from a corpus of health records using a search query. Illustrative examples of such techniques are described in further detail in U.S. patent application Ser. No. 16/908,520, entitled "Systems and Methods for Computing with Private Healthcare Data," filed Jun. 22, 2020, which is incorporated by reference herein in its entirety.

In some embodiments, filtering may be applied to the set of training data to satisfy various constraints. For example, health records associated with patients under the age of 18 may be removed from the training set. Other filtering may be performed to comply with privacy obligations or the like.

Training a neural network model, such as those described below and depicted in FIGS. 4-7, may be performed using a labeled training set of data. For example, the labeled data may be used for model training, validation, and testing. The labeled training set may include data of the same type that will eventually be used as an input to the neural network model during operation. For example, in embodiments where the neural network model used to predict a diagnosis of pulmonary hypertension based on electrocardiograms, the labeled training set may include electrocardiograms from a set of patients that have a diagnosis of pulmonary hypertension ("cases" or "positive set") and a set of patients that do not have a diagnosis of pulmonary hypertension ("controls" or "negative set"). The accuracy of these labels (e.g., the classification of diagnoses as positive/negative or as cases/controls) may have a significant impact on the performance and accuracy of the trained neural network model.

Various data from patient records may be leveraged, alone or in combination, to generate accurately labeled training sets. For example, the data may include clinical documents (including physician's notes, imaging reports, pathology reports, procedure reports), laboratory values, genetic testing results, medications and other orders, diagnosis codes, procedure codes, hospitalization history, and the like. As further described below, this data from patient records may be leveraged iteratively in order to generate accurate and relevant labeled data sets for model training, validation, and testing.

At a process 320, a neural network model is trained using the training set of health records. In some embodiments, the neural network model may be designed and trained to classify patients based on patient time series data. For example, the neural network model may be trained to diagnose patients who are at risk of having the condition of interest. In an illustrative example, the neural network model may be trained to diagnose patients with pulmonary hypertension based on ECG data.

Those skilled in the art would appreciate that a variety of types of neural network models may be used as classifiers, and that they may be trained using a variety of techniques. Examples of neural network models are described in further detail below with reference to FIGS. 4-7. Consistent with known training techniques, the training set of health records may be split into training, validation, and test sets during process 320.

One challenge associated with training neural network models is overfitting, in which the neural network model conforms to the training data too closely. As a result, overfitting reduces the performance of the neural network model when new data is introduced. In some embodiments, one or more randomization techniques may be used to make the neural network model less prone to overfitting during training. For example, one or more random transformations may be applied the time series data in the training set such that the training data changes during each iteration. Illustrative examples of random transformations may include randomly masking one or more portions of the time series data, filtering the time series data in the frequency domain (e.g., allowing frequencies in a predetermined frequency range, such as 0.5 to 50 Hz; randomly masking one or more frequency bands, such as a 1 Hz frequency band; or the like), stretching or compressing the time series data by a random zoom level, trimming the time series data by a random factor (e.g., 0.6 to 1), or the like. In some embodiments, where the training data includes time series data from a plurality of leads (e.g., multiple ECG leads), the random transformations may include randomly shuffling a set of leads at the input to the neural network model, shifting the level of the leads by different random amounts (e.g., shifting the voltage levels), or the like.

Another challenge associated with training neural network models is initialization. The initial parameters of the neural network model can impact the training time, the number of trainable parameters, the amount of training data, and the performance of the trained neural network model. In some embodiments, the initial parameters of the neural network model may be transfer learned from an independently learned self-supervised network. The self-supervised neural network may learn clustering assignments and representations based on unlabeled training data. For example, the self-supervised network may be trained based on a set of patient time series data, which may include but is not limited to the patient time series data from the labeled training set used at process 320. An example of a self-supervised network is DeepCluster v2, which is described in further detail in Caron et al., "Deep Clustering for Unsupervised Learning of Visual Features," https://arxiv.org/abs/1807.05520. In some embodiments, training may proceed in phases to address initialization issues. For example, training may include an initial warmup phase where learning rate is kept smaller than the learning rate during later phases.

In some embodiments, plurality of neural network models may be trained at process 320. For example, a different neural network model may be trained for each cohort identified at process 310. In this regard, the trained neural network models may perform more accurately compared to a neural network model in which the training data is undifferentiated or otherwise does not account for the differences among cohorts. In some embodiments, different models may be trained using diagnostic time series data (e.g., time series data captured near the time of diagnosis) versus pre-emptive time series data (e.g., time series data captured significantly before the diagnosis).

Moreover, neural network models with different architectures, training procedures, and the like may be trained at process 320. The performance of the plurality of trained models may be compared to select one or more highest performing (e.g., most accurate) models to deploy at process 330. Tables 2 and 3 below illustrates a comparison of the accuracy of preliminary diagnostic and pre-emptive models, respectively, for different cohorts. The values in the "Patient Wise AUC" and "Age Gender Wise AUC" columns correspond to an "area under curve" (AUC) metric, where a higher value indicates better diagnostic precision and recall.

TABLE 2

Patient Wise AUC

| Cohort/Set | Patient Wise AUC Mean ( 95% CI) |
|---|---|
| COHORT 1: | 0.7613 |
| RHC >= 25 mmHg vs RHC < 21 mmHg | (0.7527 <-> 0.7695) |
| COHORT 2: | 0.7502 |
| RHC >= 21 mmHg vs RHC < 21 mmHg | (0.7442 <-> 0.7583) |
| COHORT 3_26: | 0.9107 |
| RHC >= 25 mmHg vs RHC < 21 mmHg + TRV <= 2.6 m/s | (0.9093 <-> 0.912) |
| COHORT 3: | 0.9059 |
| RHC >= 25 mmHg vs RHC < 21 mmHg + TRV <= 2.8 m/s | (0.9047 <-> 0.9069) |
| COHORT 4_26: | 0.8997 |
| RHC >= 21 mmHg vs RHC < 21 mmHg + TRV <= 2.6 m/s | (0.8982 <-> 0.901) |
| COHORT 4: | 0.8927 |
| RHC >= 21 mmHg vs RHC < 21 mmHg + TRV <= 2.8 m/s | (0.8913 <-> 0.8944) |
| COHORT 5_26: | 0.8847 |
| TRV >= 3.4 m/s vs TRV <= 2.6 m/s | (0.8831 <-> 0.8867) |
| COHORT 5: | 0.8701 |
| TRV >= 3.4 m/s vs TRV <= 2.8 m/s | (0.8688 <-> 0.8716) |
| COHORT 6_26: | 0.8389 |
| TRV >= 2.8 m/s vs TRV < 2.6 m/s | (0.8375 <-> 0.8402) |
| COHORT 6: | 0.8193 |
| TRV >= 2.8 m/s vs TRV <= 2.8 m/s | (0.8183 <-> 0.8212) |

TABLE 2-continued

Age Gender Wise AUC

| Cohort/Set | Age Gender Wise AUC Mean ( 95% CI) |
|---|---|
| COHORT 1: | 0.7381 |
| RHC >= 25 mmHg vs RHC < 21 mmHg | (0.7363 <-> 0.7396) |
| COHORT 2: | 0.7228 |
| RHC >= 21 mmHg vs RHC < 21 mmHg | (0.7206 <-> 0.725) |
| COHORT 3_26: | 0.8898 |
| RHC >= 25 mmHg vs RHC < 21 mmHg + TRV <= 2.6 m/s | (0.889 <-> 0.8905) |
| COHORT 3: | 0.8935 |
| RHC >= 25 mmHg vs RHC < 21 mmHg + TRV <= 2.8 m/s | (0.8926 <-> 0.8943) |
| COHORT 4_26: | 0.8821 |
| RHC >= 21 mmHg vs RHC < 21 mmHg + TRV <= 2.6 m/s | (0.8814 <-> 0.8828) |
| COHORT 4: | 0.8828 |
| RHC >= 21 mmHg vs RHC < 21 mmHg + TRV <= 2.8 m/s | (0.882 <-> 0.8836) |
| COHORT 5_26: | 0.8729 |
| TRV >= 3.4 m/s vs TRV <= 2.6 m/s | (0.8722 <-> 0.8736) |
| COHORT 5: | 0.8591 |
| TRV >= 3.4 m/s vs TRV <= 2.8 m/s | (0.8585 <-> 0.8596) |
| COHORT 6_26: | 0.8347 |
| TRV >= 2.8 m/s vs TRV < 2.6 m/s | (0.8327 <-> 0.8368) |
| COHORT 6: | 0.813 |
| TRV >= 2.8 m/s vs TRV <= 2.8 m/s | (0.8112 <-> 0.8147) |

TABLE 3

Patient Wise AUC

| Cohort/Set | Patient Wise AUC Mean ( 95% CI) |
|---|---|
| COHORT 1: | 0.677 |
| RHC >= 25 mmHg vs RHC < 21 mmHg | (0.6627 <-> 0.6946) |
| COHORT 2: | 0.6523 |
| RHC >= 21 mmHg vs RHC < 21 mmHg | (0.6353 <-> 0.6706) |
| COHORT 3_26: | 0.859 |
| RHC >= 25 mmHg vs RHC < 21 mmHg + TRV <= 2.6 m/s | (0.853 <-> 0.8643) |
| COHORT 3: | 0.851 |
| RHC >= 25 mmHg vs RHC < 21 mmHg + TRV <= 2.8 m/s | (0.8449 <-> 0.8572) |
| COHORT 4_26: | 0.8386 |
| RHC >= 21 mmHg vs RHC < 21 mmHg + TRV <= 2.6 m/s | (0.8322 <-> 0.843) |
| COHORT 4: | 0.8381 |
| RHC >= 21 mmHg vs RHC < 21 mmHg + TRV <= 2.8 m/s | (0.8335 <-> 0.8441) |
| COHORT 5_26: | 0.75 |
| TRV >= 3.4 m/s vs TRV <= 2.6 m/s | (0.744 <-> 0.7569) |
| COHORT 5: | 0.7296 |
| TRV >= 3.4 m/s vs TRV <= 2.8 m/s | (0.7229 <-> 0.739) |
| COHORT 6_26: | 0.7611 |
| TRV >= 2.8 m/s vs TRV < 2.6 m/s | (0.7558 <-> 0.7655) |
| COHORT 6: | 0.7312 |
| TRV >= 2.8 m/s vs TRV <= 2.8 m/s | (0.7274 <-> 0.7341) |

Age Gender Wise AUC

| Cohort/Set | Age Gender Wise AUC Mean ( 95% CI) |
|---|---|
| COHORT 1: | 0.6764 |
| RHC >= 25 mmHg vs RHC < 21 mmHg | (0.6665 <-> 0.6858) |
| COHORT 2: | 0.651 |
| RHC >= 21 mmHg vs RHC < 21 mmHg | (0.6436 <-> 0.6604) |
| COHORT 3_26: | 0.8313 |
| RHC >= 25 mmHg vs RHC < 21 mmHg + TRV <= 2.6 m/s | (0.8265 <-> 0.8354) |
| COHORT 3: | 0.8348 |
| RHC >= 25 mmHg vs RHC <2 1 mmHg + TRV <= 2.8 m/s | (0.8319 <-> 0.8384) |

TABLE 3-continued

| | |
|---|---|
| COHORT 4_26: | 0.8189 |
| RHC >= 21 mmHg vs RHC <2 1 mmHg + TRV <= 2.6 m/s | (0.8153 <-> 0.8217) |
| COHORT 4: | 0.8163 |
| RHC >= 21 mmHg vs RHC < 21 mmHg + TRV <= 2.8 m/s | (0.8122 <-> 0.8198) |
| COHORT 5_26: | 0.7244 |
| TRV >= 3.4 m/s vs TRV <= 2.6 m/s | (0.7192 <-> 0.7291) |
| COHORT5: | 0.6973 |
| TRV >= 3.4 m/s vs TRV <= 2.8 m/s | (0.6905 <-> 0.7036) |
| COHORT 6_26: | 0.7191 |
| TRV >= 2.8 m/s vs TRV < 2.6 m/s | (0.7163 <-> 0.7217) |
| COHORT 6: | 0.6964 |
| TRV >= 2.8 m/s vs TRV <= 2.8 m/s | (0.6939 <-> 0.699) |

The configuration of the neural network model used to generate the data in Tables 2 and 3 above was a single-branch convolutional model (i.e., time series data from each of the 12 ECG leads was combined and provided as an input to a single convolutional branch), did not include inputs for age/gender or spectrogram data, included residual connections, and segmented the time-series data into overlapping two-second windows. It is to be understood that this configuration is merely illustrative, and that a variety of other configurations of the neural network are possible, several of which are discussed below with reference to FIGS. 4-7.

At a process 330, the trained neural network model is executed to diagnose a health condition based on patient time series data. In some embodiments, the neural network model may receive the patient time series data as an input and may output a determination of whether the patient is at risk of having the health condition. The neural network model may additionally receive as inputs data other than the time series data, such as the patient's age, sex, ethnicity, and other relevant information associated with the patient. The output of the neural network model may include a numerical score, a classification (e.g., "high risk" or "low risk"), or another suitable indicator or combination of indicators to identify whether the patient is at risk of having the health condition.

In some embodiments, executing the trained neural network model may include pre-processing the time series data. For example, the time series data may be received as a vector representation, in which case the pre-processing may include converting the time series data to a spectrogram representation. One or both of the vector and spectrogram representations may then be provided as an input to the neural network model. In some embodiments, the pre-processing may include extracting one or more discrete metrics based on the time series data, such as a QT interval of an ECG waveform. The discrete metrics may be provided as additional inputs to the neural network model. In some embodiments, the pre-processing may include segmenting the time series data into time windows. For example, where the original time series data spans a particular measurement duration (e.g., 10 seconds), the time series data may be segmented into smaller time windows (e.g., two seconds). The windows may be overlapping, e.g., a two-second window centered at each second of the time series data (0-2 s, 1-3 s, 2-4 s, etc.). The size of the window may correspond to a duration long enough to capture complete pulse cycle, thereby retaining the accuracy of the neural network model while improving its training time and performance.

In some embodiments, the trained neural network model may be executed in a computing environment apart from that used to train the neural network model. For example, the trained neural network model may be deployed to a cloud computing environment, where third parties may upload patient time series data to obtain a diagnosis. In some embodiments, the trained neural network may be deployed and executed locally with respect to a medical instrument used to capture the time series data, such as an ECG monitor.

At an optional process 340, a plurality of outputs of the trained neural network model are aggregated to generate an aggregate diagnosis of the health condition. For example, consistent with embodiments in which the time series data is segmented into smaller time windows (e.g., two second windows), the outputs of the neural network model for each time window of the time-series data may be aggregated. In some embodiments, the aggregation may be performed by averaging numerical scores output by the neural network model for each time window (or otherwise computing a suitable aggregate score based on the plurality of scores).

Figure 4:
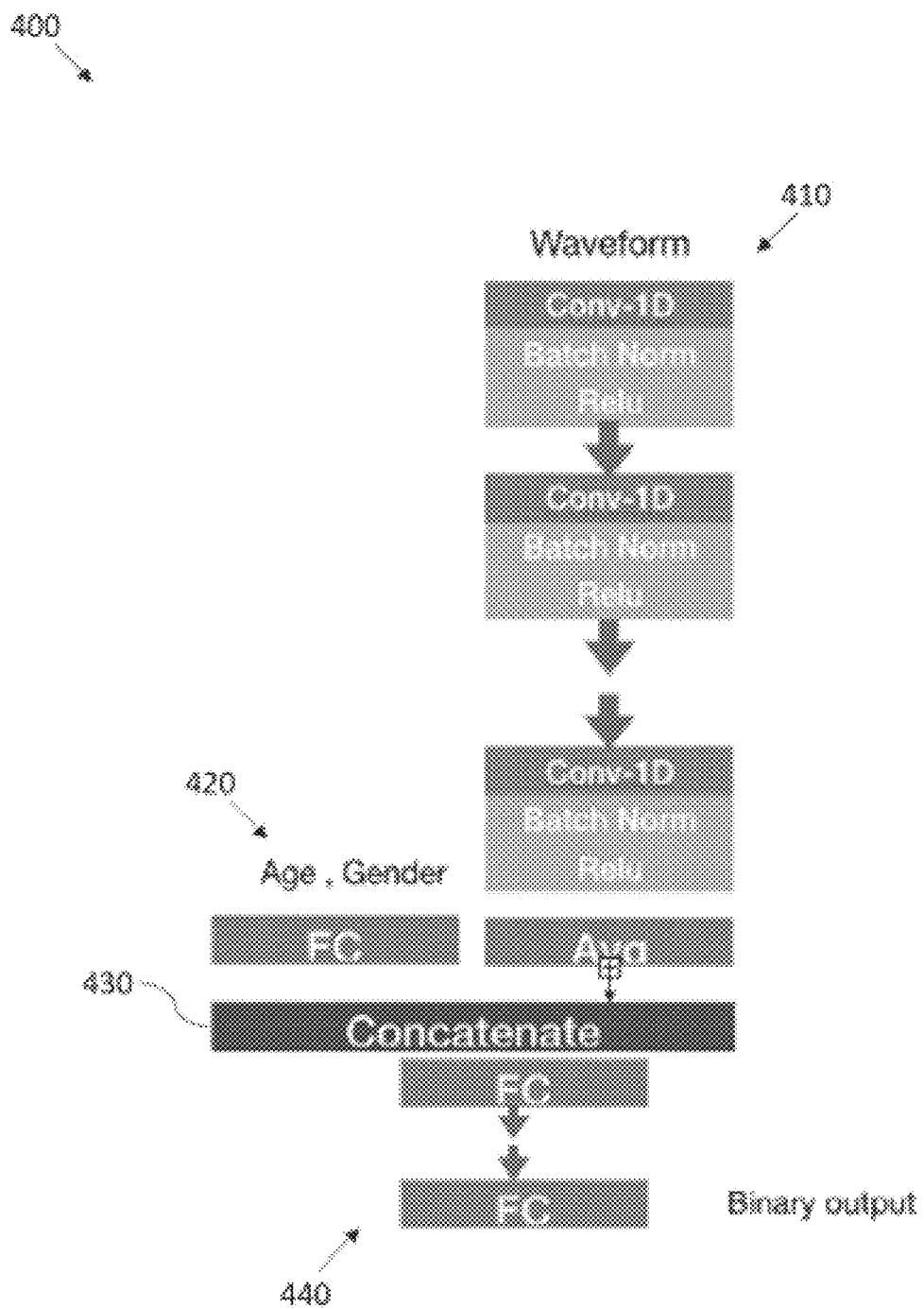
FIG. 4 is a simplified diagram of a neural network model with single branch convolution according to some embodiments.

FIG. 4 is a simplified diagram of a neural network model 400 with single branch convolution according to some embodiments. In some embodiments, neural network model 400 may be used in method 300 to diagnose a health condition based on patient time series data.

Neural network model 400 includes a convolution branch 410 that processes input time series data (e.g., a waveform, such as an ECG waveform). Convolution branch 410 includes one or more convolution layers, e.g., 1-dimensional convolutional layers ("Conv-1D") when processing a waveform representation of the time series data. Convolutional branch 410 may include various other types of layers in addition to the one or more convolution layers, such as a normalization layer (e.g., a batch normalization layer ("batch norm")), an activation function (e.g., the rectified linear activation function ("ReLU")), and pooling layer (e.g., an average pooling layer ("average")), a fully connected layer ("FC"), or the like. Neural network model 400 optionally includes one or more additional branches 420 to process inputs other than the time series data, such as the patient's age and gender, which may likewise include various types of layers such as those illustratively identified above. Such inputs may be included when it is determined that they are clinically relevant and/or improve the accuracy of neural network model 400, and omitted otherwise. The additional branches 420 may not use convolution layers.

The outputs of convolution branch 410 and additional branches 420 are concatenated at a concatenation layer 430 ("Concatenate"). One or more output layers 440 may follow concatenation layer 430 to produce the output of neural network model 400.

Although neural network model 400 is depicted with a single convolution branch 410 for simplicity, it is to be understood that neural network model 400 may include additional convolution branches that are concatenated at concatenation layer 430. For example, ECG time series data may include a plurality of waveforms corresponding to different leads of the ECG system (e.g., 12 leads in a standard configuration). In some embodiments, time series data from each lead may be provided to a separate convolution branch (e.g., neural network model 400 may include 12 convolution branches, one for each lead). Alternatively, the time series data from the leads may be combined and provided to a number of convolution branches that is less than the number of leads (e.g., the data from each of the 12 leads may be combined and provided as an input to a single branch). For example, time series data from more than one lead may be appended together to form a combined array of time series data that is provided as an input to a convolution branch.

Figure 5:
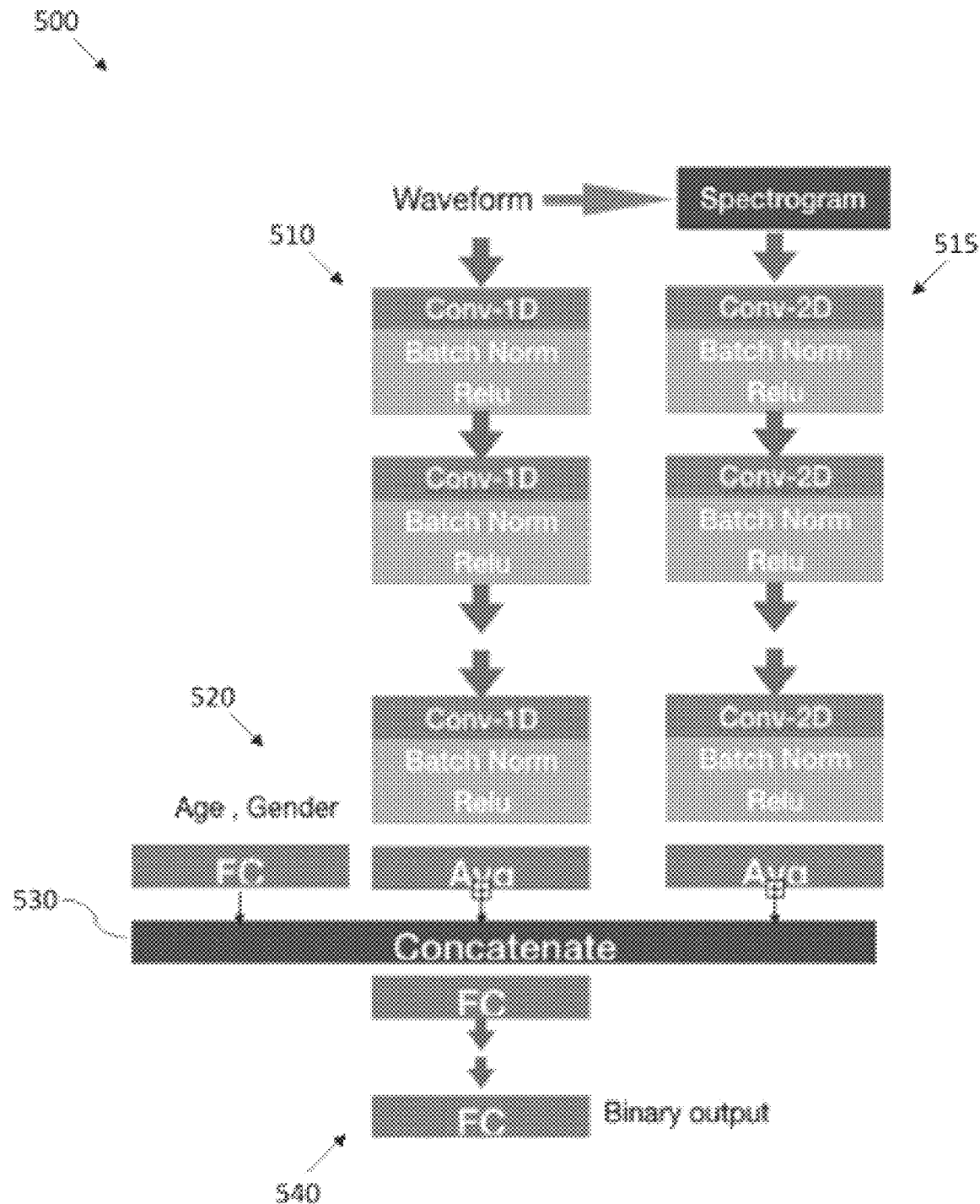
FIG. 5 is a simplified diagram of a neural network model with multiple branch convolution according to some embodiments.

FIG. 5 is a simplified diagram of a neural network model 500 with multiple branch convolution according to some embodiments. In some embodiments, neural network model 500 may be used in method 300 to diagnose a health condition based on patient time series data.

Neural network model 500 includes branches and layers similar to those of neural network model 400, including a first convolutional branch 510 for processing input time series data in a 1-dimensional waveform representation, additional branches 520 for processing inputs other than the time series data, a concatenation layer 530 for concatenating the outputs of branches 510-520, and one or more output layers 540 to generate the output result.

Relative to neural network model 400, neural network model 500 further includes a second convolution branch 515 that processes a second representation of the input time series data. For example, as depicted in FIG. 5, second convolution branch 515 processes a spectrogram representation of the input time series data. Because a spectrogram includes two-dimensional data, second convolution branch 515 includes one or more two-dimensional convolution layers. Like first convolution branch 510, the output of second convolution branch 515 is concatenated along with the other branches 510-520 at convolution layer 530.

Figure 6:
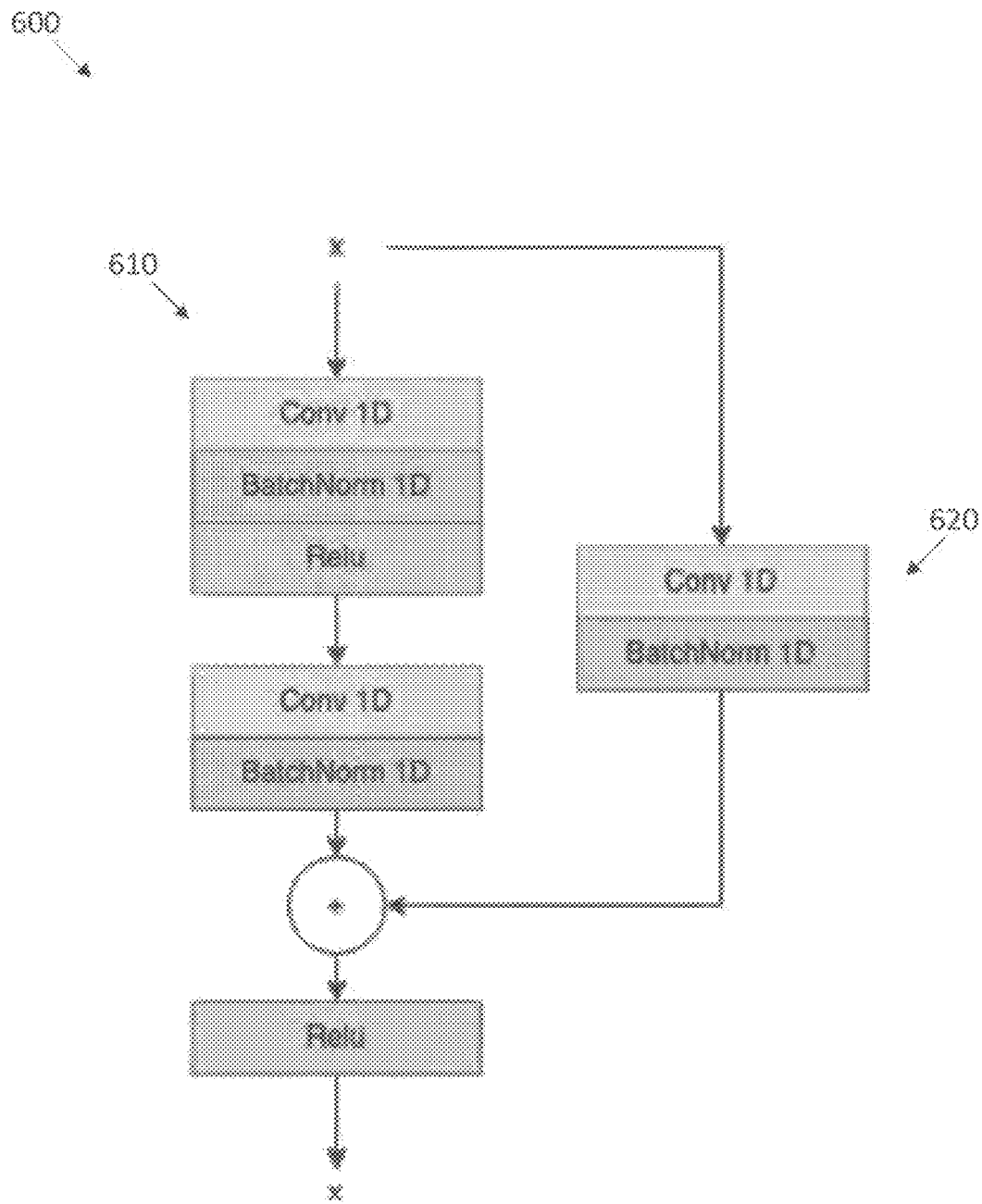
FIG. 6 is a simplified diagram of a convolution block of a neural network model with residual connections according to some embodiments.

FIG. 6 is a simplified diagram of a convolution block 600 of a neural network model with residual connections according to some embodiments. In some embodiments, convolution block 600 may be used in neural network model 400 or neural network model 500 as part of a convolution branch, e.g., convolutional branches 410, 510, or 515. Convolutional block 600 illustrates a residual connection 620 with a stride of two, i.e., a layer that bypasses two layers of the main branch 610. As would be appreciated by those skilled in the art, including residual connections in the convolutional branch may significantly improve model performance and accuracy.

Figure 7A:
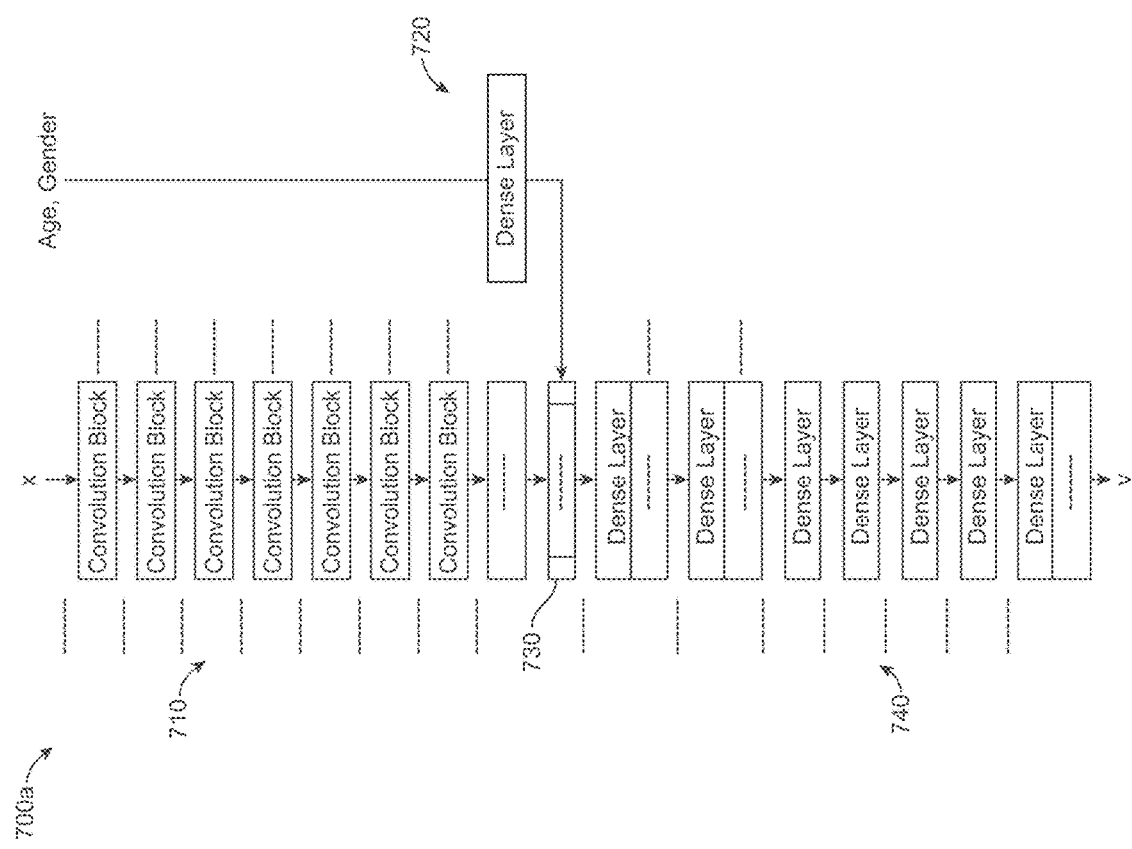
FIGS. 7A and 7B are simplified diagrams showing exemplary implementations of a neural network model according to some embodiments.
Figure 7B:
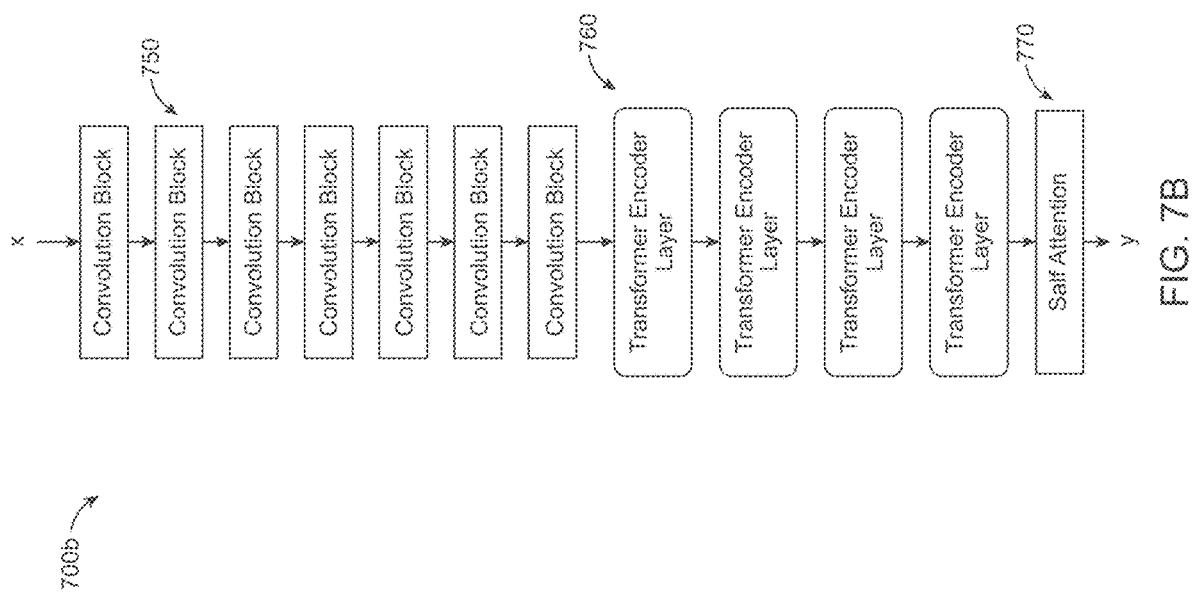

FIGS. 7A and 7B are simplified diagrams showing implementation details of respective neural network models 700a and 700b according to some embodiments. In some embodiments, neural network model 700a, neural network model 700b, or a combination thereof, may be used to implement neural network model 400. With the addition of a second convolutional branch, neural network models 700a or 700b may also be used to implement neural network model 500.

Neural network model 700a includes branches an layers similar to those of neural network model 400, including a convolutional branch 710 for processing input time series data (x), an additional branch 720 for processing inputs other than the time series data (age and gender), a concatenation layer 730 for concatenating the outputs of branches 710-720, and output layers 740 to generate the output prediction (y). Illustrative types and parameters for each layer are identified in the figure.

Neural network model 700b includes one or more convolutional blocks 750 and one or more transformer encoder layers 760. As shown in FIG. 7B, the transformer encoder layers 760 follow the convolutional blocks 750. A self-attention layer 770 receives an output from transformer encoder layers 760 and generates the output prediction (y). However, it is to be understood that other arrangements of the layers in FIG. 7B are possible, including rearranging the layers, adding branches or otherwise modifying the network structure, adding or substituting different types of layers not shown in FIG. 7B, or the like. Relative to neural network model 700a, the use of transformer encoder layers 760 in neural network model 700b may increase interactions across different portions of the input time series data (x) when generating output prediction (y). In some embodiments, the convolutional blocks 750 may generate a sequence of encodings that each represent a portion of the input time series data (x) (e.g., a particular time period that is shorter than the full duration of the input time series data). The encodings may each have a fixed size. The transformer encoder layers 760 may receive the sequence of encodings to generate the output prediction (y). Illustrative examples of transformer encoder layers 760 are described in further detail, for example, in Vaswani et al., "Attention is All You Need," arXiv:1706.03762, which is incorporated by reference herein in its entirety.

It is to be understood the FIGS. 4-7 are merely examples, and many alternative configurations of the neural network models are possible. For example, the neural network models may include additional or fewer branches, or layers within branches, and the types of each layer may be different. The points at which branches are concatenated with other branches may vary. In some embodiments, different representations of the input time series data may be used, including representations other than one-dimensional waveforms and two-dimensional spectrograms.

Figure 8:
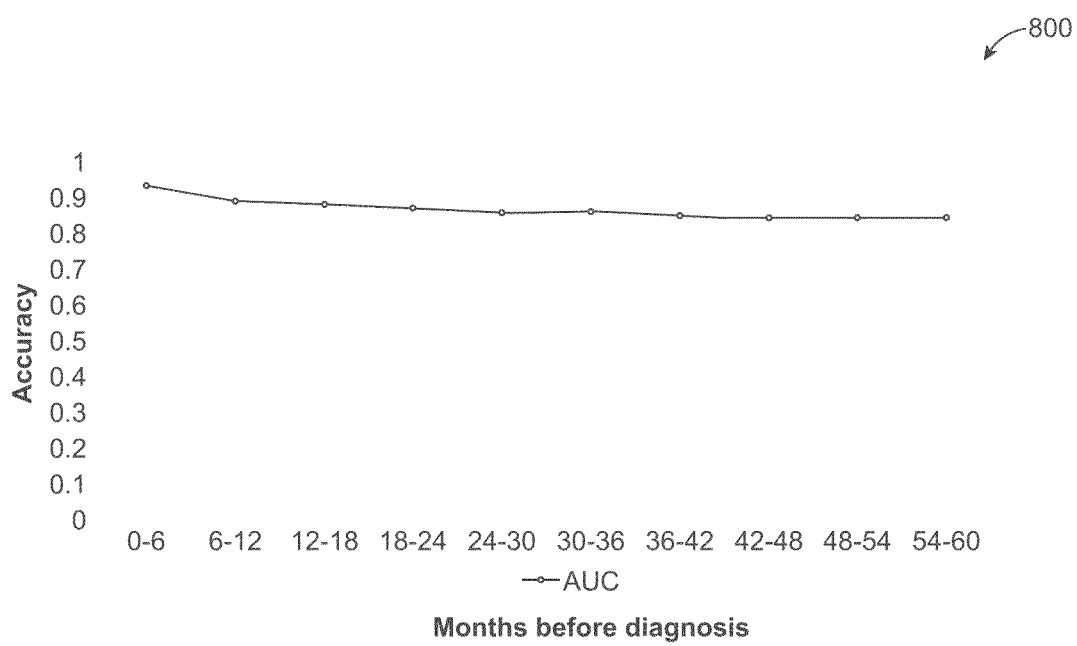
FIG. 8 is a simplified diagram showing a graph of model accuracy using time-series data captured a given number of months before a pulmonary hypertension diagnosis according to some embodiments.

FIG. 8 is a simplified diagram showing a graph 800 of model accuracy using time-series data captured a given number of months before a pulmonary hypertension diagnosis according to some embodiments. The neural network model and patient data used to generate graph 800 corresponds to patients from cohort 3, as identified in Tables 1-3 above. As shown in graph 800, there is not a significant drop-off in AUC (which reflects precision and recall of the model) even for data collected as much as five years (60 months) prior to a pulmonary hypertension diagnosis.

Figure 9:
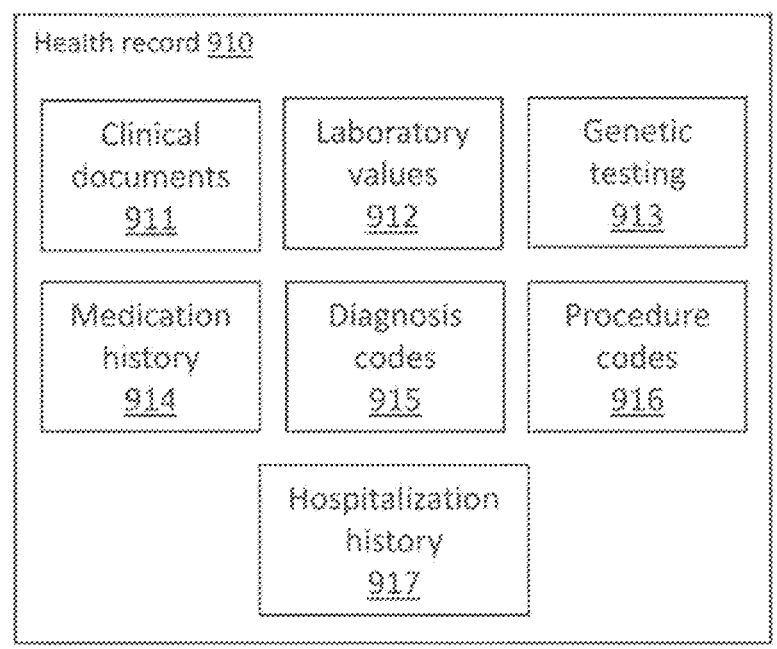
FIG. 9 is a simplified diagram of a data flow illustrating components of a patient health record that may be used to generate a training data set according to some embodiments.
Figure 9:
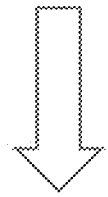
Figure 9:
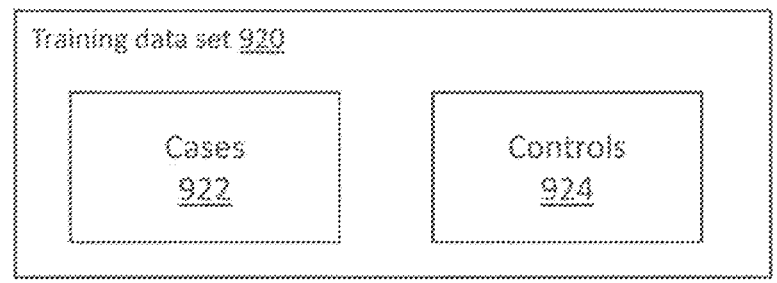

FIG. 9 is a simplified diagram of a data flow 900 illustrating components 911-917 of a patient health record 910 that may be used to generate a training data set 920 according to some embodiments. Based on an analysis of the patient health record 910, the patient may be classified as a case 922 or a control 924 within the training data set 920, or may be excluded from training data set 920.

Clinical documents 911 may include one or more documents produced during the clinical care of a patient that contain unstructured text authored or dictated by a member of a patient's care team. Clinical documents 911 may include physician's notes, imaging reports, pathology reports, procedure reports, as well as notes produced by non-physician members of a patient's care team such as nurses, physical therapists, occupational therapists, social workers, dieticians, and case managers. In some embodiments, the diagnosis of disease may be obtained from clinical documents by applying natural language processing (NLP) algorithms, transformer-based neural network models, and/or the like. These models may determine if a physician or care team member is documenting that the patient is diagnosed with a certain disease. Illustrative embodiments of processes for obtaining a diagnosis of a disease from clinical documents using a process of "augmented curation" are described in further detail in U.S. patent application Ser. No. 16/908,520, entitled "Systems and Methods for Computing with Private Healthcare Data," filed Jun. 22, 2020, which is hereby incorporated by reference in its entirety.

The diagnosis of a disease may be based on a comprehensive assessment of medical and physiological data and clinical assessment (history, physical exam) by a physician. This comprehensive assessment may be based on unstructured notes, structured data sources (such as diagnosis codes or laboratory values), or a combination thereof. The unstructured clinical documents 911 may therefore provide complementary information to structured data sources within health record 910. The models may also identify whether a physician or care team member has determined that a patient does not have a certain disease, might have a certain disease, or has a family history of a certain disease.

In the illustrative case of pulmonary hypertension, clinical documents 911 may be used to identify patients that have been diagnosed with pulmonary hypertension by a qualified individual or team that has assessed, for example, a patient's history and symptoms as well as medical and physiological data such has right heart catheterization and echocardiogram results. Similarly, when developing a control cohort 924 (e.g., a set of patients that have not been diagnosed with pulmonary hypertension), the clinical documents 911 may be processed to identify a lack of physician documentation of pulmonary hypertension or family history of pulmonary hypertension.

In the illustrative case of light chain amyloidosis ("AL amyloidosis"), patient diagnosis is typically complex and may involve satisfying one or more criteria, such as that there be no better explanation for the constellation of signs and symptoms that a patient is presenting with than AL amyloidosis. A qualified individual or team may check these criteria by assessing symptoms, comorbid diseases, laboratory results, pathology results, or the like. Thus, obtaining a diagnosis of AL amyloidosis from the clinical documents 911 rather than (or in addition to) structured data sources may synthesize a greater amount of relevant information, thereby improving the identification of cases for neural network model development. Another criteria may be that the patient have AL amyloidosis that has been confirmed by biopsy at the institution from which the training data originates (e.g., as reflected in a pathology report). In this manner, the impact of events that occurred outside of the institution, including treatment and disease sequelae, on model training, validation, and testing is minimized. Conversely, the control cohort 924 may be made more robust by including a criteria that a patient not have a diagnosis of light chain amyloidosis, or have explicit absence of light chain amyloid on a relevant biopsy. As outlined below, laboratory values 912 may be used to further add to the robustness of the control cohort 924.

Laboratory values 912 and other structured physiological data (e.g., genetic testing 913) may include laboratory testing done on clinical samples extracted from a patient, physiological studies in which results are reported in a structured format, or the like. Examples of laboratory tests include blood tests (serum, plasma), urine tests, body fluid tests, cerebrospinal fluid tests. Laboratory tests also include gene panels for certain diseases. Examples of physiological studies which are reported in structured form include echocardiography, heart catheterization, vital signs, spirometry, and pulmonary function tests. Such laboratory values 912 may be analyzed to either increase or decrease the likelihood that a disease is present in the case or control cohort, respectively, resulting in more accurate labels for the case 922 and control 924 cohorts and thereby improving the neural network model's ability to discriminate between health and disease.

For example, when developing case 922 and control 924 cohorts for training a neural network model to predict a diagnosis of AL amyloidosis, laboratory values 912 may help define a group of patients that most likely do not have AL amyloidosis. Laboratory values are relevant in the context of AL amyloidosis because the absence of a diagnosis of AL amyloidosis in a patient's diagnosis code history (e.g., diagnosis codes 915) or clinical notes (e.g., clinical documents 911) is often insufficient to rule out AL amyloidosis, e.g., because the diagnosis of AL amyloidosis is often delayed or missed due to the nonspecific nature of symptoms. The diagnosis of AL amyloidosis is complex and may be based on evidence of organ damage related to the deposition of proteotoxic light chain amyloid. Organ damage is often assessed using blood tests. For example: serum troponin, B-type natriuretic peptide (BNP), N-terminal prohormone of brain natriuretic peptide (NT-proBNP) are often used to detect heart injury; serum creatinine is often used to assess for kidney injury; coagulation labs and liver functional tests are used to assess for liver injury; and serum thyroid stimulating hormone (TSH) is used to assess thyroid damage. By selecting patients in the control cohort 924 that have normal values for these laboratory tests (in addition to not having a diagnosis of AL amyloidosis), the likelihood that patients in the cohort do not have undiagnosed AL amyloidosis is increased. Accordingly, laboratory tests that are performed more frequently in the AL amyloidosis population when compared to other patients, and their normal and abnormal ranges (e.g., a value or range that would be consistent with organ damage), may be identified. Patient in the control cohort 924 may include patients with normal values for those laboratory tests.

Medication history 914 may be obtained by examining a patient's order history or inpatient medication administration history (MAR). Clinical documents 911 may also be examined to identify physician-documented medication history (which may include aspects of the medication history 914 that are not present in the order history or MAR). A patient's medication history 914 may be used to refine case 922 and control 924 cohort definition. For example, if a patient receives a medication that alters the physiology associated with a certain disease, then it may benefit model training to remove that patient from the training data set 920 (either from the case 922 or control 924 cohorts, or both). In the case of pulmonary hypertension, patients who received drugs indicated for pulmonary hypertension prior to first right heart catheterization may be removed from the case cohort 922 because it is plausible that these patients had artificially lowered pulmonary arterial pressures, and therefore altered cardiopulmonary physiology, prior to diagnosis by right heart catheterization.

Medication history 914 may also be used to assess differences between case 922 and control 924 cohorts. For example, upon defining case 922 and control 924 cohorts, medication history 914 may be compared between the cohorts in order to characterize the treatments that these patients received. In some embodiments, it may be desirable to match case 922 and control 924 cohorts according to medications received. In order to do so, an iterative approach may be employed in which case 922 and control 924 cohorts are generated, medications histories 914 are examined for significant enrichments in cases versus controls or vice versa, medications are selected for matching, and the process is repeated until clinically relevant matching has been obtained.

Diagnosis codes 915 are diagnoses that have been coded in a structured form. Standardized coding systems may be used, such as the International Classification of Diseases (ICD) or the Systematized Nomenclature of Medicine Clinical Terms (SNOMED-CT) coding systems. Although such codes may be inaccurate, they may provide a rapid and flexible way to characterize and refine cohorts. In order to characterize and refine cohorts, an iterative process may be employed in which: 1) case 922 and control 924 cohorts are selected, 2) a neural network model is trained and tested, 3)

cohorts of true positives, false positives, true negatives, and false negatives are generated, 4) diagnosis code histories 915 for each are examined and significant enrichments between pairwise comparisons of each cohort are obtained, 5) enrichments are selected as "exclusion criteria" so that model performance improves, and 6) the process is repeated with the refined cohort. Diagnosis codes 915 may also be selected for a cohort matching process based on medication history 914 as described above.

Procedure codes 916 may identify procedures that a patient has undergone, and may be recorded in a structured form via the use of coding systems such as the Current Procedural Terminology (CPT) coding system, the International Classification of Diseases Procedural Coding System (ICD-PCS), Healthcare Common Procedure Coding System (HCPCS), or the like. Procedure codes 916 can be used to identify sets of patients who have undergone procedures that may impact their physiology. For example, the implantation of a cardiac pacemaker and active pacing fundamentally alters the characteristics of an electrocardiogram waveform due to the added, artificial modulation of heart rate and rhythm. Thus, procedure codes 916 may be used to remove patients who have received a pacemaker from both cases 922 and controls 914. The resultant set of waveforms used for model training more accurately reflect the natural physiology of the cohorts.

In some embodiments, a patient's hospitalization history 917 may provide information about the severity of a patient's illness. For example, in clinical trials for heart failure, a common primary outcome measure is the time to first hospitalization for acute heart failure following an intervention. Thus, a patient's hospitalization history 917 may be leveraged to develop neural network models that predict hospitalization following a particular intervention. For example, a model that predicts which patients will be hospitalized (and which will not) for acute heart failure following the administration of a drug that treats heart failure may be developed. Such a model would help identify those patients that would be most likely to benefit from the drug.

The hospitalization history 917 may also be leveraged to develop neural network models that subset patients by severity of illness prior to intervention in order to generate more robust cohorts. For example, in the case of pulmonary hypertension, a neural network model that can predict a diagnosis of pulmonary hypertension in the primary care setting may be developed. Thus, patient data that comes from inpatient hospitalizations may be excluded in order to optimize the model for performance in its target setting.

FIGS. 10A-10H are simplified diagrams showing experimental data associated with the techniques of FIGS. 1-9 when applied to the diagnosis of pulmonary hypertension according to some embodiments. Pulmonary hypertension (PH) is a life-threatening disease estimated to affect 1% of the global population and up to 10% of patients over 65 years of age. The timely diagnosis of PH is imperative not only for effective therapeutic intervention but also to amplify the odds of survival. Multiple studies suggest that earlier diagnosis, even a few months, can lead to dramatic increases in quality of life and lifespan extension. However, the symptoms of PH are non-specific and very similar to the symptoms seen in other common diseases, including asthma, chronic obstructive pulmonary disease (COPD), and heart failure. This makes the suspicion of PH low within ambulatory care settings, and thus timely referral to pulmonologists or cardiologists who can confirm diagnosis is critical. Currently, diagnosis is often delayed, with an average time from onset of symptoms to diagnosis of 2.5 years and up to 4 years in some cases primarily due to delayed referral to PH specialists. Indeed, because the gold standard for the definitive diagnosis of PH is right heart catheterization (RHC), an invasive procedure that entails non-negligible risks, physicians often hesitate to proceed until all other diseases have been sequentially ruled out. An algorithm applied to ECG, a non-invasive procedure, in the diagnostic workup of PH may help detect PH and possibly stratify patients based on the risk of PH, allowing earlier diagnosis and intervention.

Consistent with the techniques of FIGS. 1-9, multiple cohorts were generated using a combination of structured and/or unstructured data from electronic medical records, more specifically the mean pulmonary arterial pressure (mPAP) measured during RHC, tricuspid regurgitation velocity (TRV) measured during echocardiogram, and the physician notes. The resulting cohorts are shown in FIG. 10A. RHC is the gold standard for PH diagnosis, with an mPAP 21 mmHg denoting PH, recently lowered from the previous threshold of mPAP 25 mmHg. Both thresholds were used for cohort definitions (Cohorts 1-4, 8-9) with a slight variant (mPAP>20 mmHg) used for Cohort 12. TRV measurements are less conclusive; while TRV<2.8 m/s indicates the absence of PH and TRV>3.4 m/s indicates its presence, there is an intermediate range for which diagnosis is inconclusive using TRV alone and other measurements or diagnostic tests must be considered. TRV alone was used to define some cohorts (Cohorts 5-6, 10-11), but in other cases TRV was also used to supplement the negative cohort when RHC provided limited patient counts (Cohorts 3-4, 8-9). Finally, some cohorts used a TRV<2.6 m/s as a more stringent negative control criterion.

Using techniques described above with reference to FIG. 9, each of these cohorts were further refined using laboratory values (e.g., laboratory values 912), medications and other orders (e.g., medication history 914), diagnosis codes (e.g., diagnosis codes 915), procedure codes (e.g., procedure codes 916), and hospitalization history (e.g., hospitalization history 917). For example, patients on PH medication prior to diagnosis via RHC or echo, patients with potentially confounding comorbidities, patients who underwent transplants or surgical cardiac procedures, patients exhibiting PH only following exercise or drug challenge, and patients with acute cardiac monitoring were all independently or in combination considered for exclusion during the following algorithm development and testing. Similarly, testing was also performed on subsets of patients with one or more of the following inclusion criteria: patients with pre-capillary, post-capillary, or combined pre- and post-capillary PH, patients diagnosed with pulmonary arterial hypertension (PAH) in their physician notes, patients receiving PAH medications, patients who received 2 or more ECGs within a 6-month period, and patients within certain age ranges.

Additionally, one cohort was generated using diagnosis extracted from the clinical notes, coupled with echo measurements to test the capabilities of augmented curation (Cohort 7). Note that this cohort was generated using a subset of patients with echocardiogram measurements, which accounts for the lower number of PH patients. As a first step toward this end, a positive control cohort of 1,630 patients was identified, hereafter referred to as the Initial PH Cohort. To expand this cohort, an additional 19,504 patients that contained the term "pulmonary hypertension" within their notes were identified, hereafter referred to as the Potential PH Cohort.

A BERT model was trained to classify the sentiment regarding a PH diagnosis. As a first step toward creating a BERT model for diagnosis, the top 250 phenotypes most closely associated to "pulmonary hypertension" were determined and sentences from the corpus of clinical notes were extracted for these phenotypes. Sentences were classified by qualified individuals into the following categories, with examples shown in FIG. 10B: positive (YES), negative (NO), suspected (MAYBE), and alternate context (OTHER). These categories are non-limiting, and additional categories can be added to this training set to support increased model granularity, e.g. separating out family history and/or disease risk resulting from medication (both encompassed by OTHER in the illustrative categories above).

A multi-user software application was developed for sentence tagging, with a user interface that improved efficiency while also tracking the changes made across multiple users. The first model was generated on 11,433 sentences and had on overall accuracy—calculated as the fraction of labels the model correctly predicted over the total sentences—of 0.85. The user interface enabled the user to review tagged sentences that the model classified incorrectly and could also be used to run the model on an untagged set of sentences, again improving downstream efficiency of the augmented curation. As discussed above, embodiments of augmented curation processes are described in further detail in U.S. patent application Ser. No. 16/908,520. As shown in FIG. 10C, with multiple cycles of augmented curation, the accuracy of the model improved from 0.85 to 0.936.

Because the model was trained on 250 different PH-related phenotypes, the sentences used to train this model were primarily discussing diseases related to cardiology, pulmonology, and metabolic disorders. Given the breadth of the phenotypes already captured by the model, it is robust enough to scale to additional therapeutic areas, ranging from COVID-19 to oncology, with retraining using a relatively small amount of new training data (e.g., 1000-3000 sentences). In some embodiments, additional curation may be performed to capture specific language or context in that particular field.

Figure 10D:
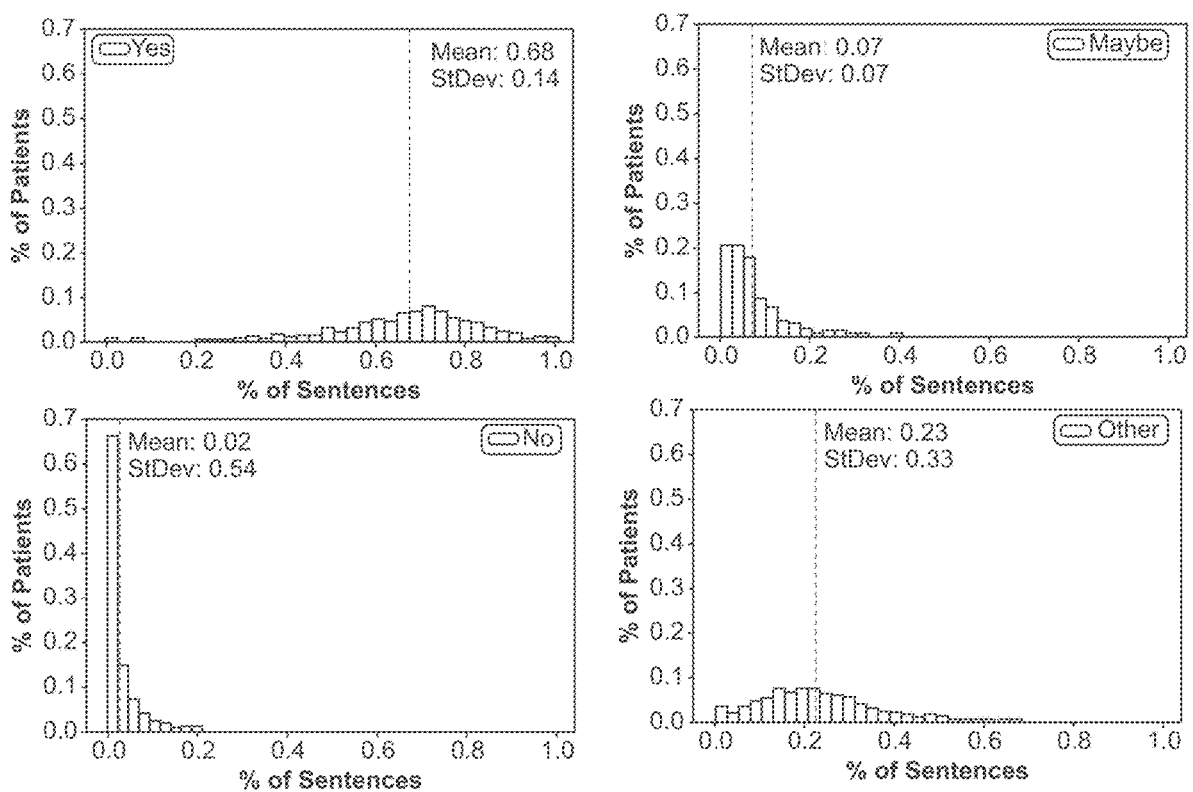

Before running the BERT model on the Potential PH Cohort to identify additional PH patients, it was run on the Initial PH Cohort to assess the distribution of sentence sentiment for a positive control. Here, approximately 180,000 sentences for these patients containing the term "pulmonary hypertension" were classified by the model. As shown in FIG. 10D, on average 68% of sentences were classified as YES sentiment, only 2% as NO, 7% as MAYBE, and 23% as OTHER, an excellent validation of our model and positive cohort.

Figure 10E:
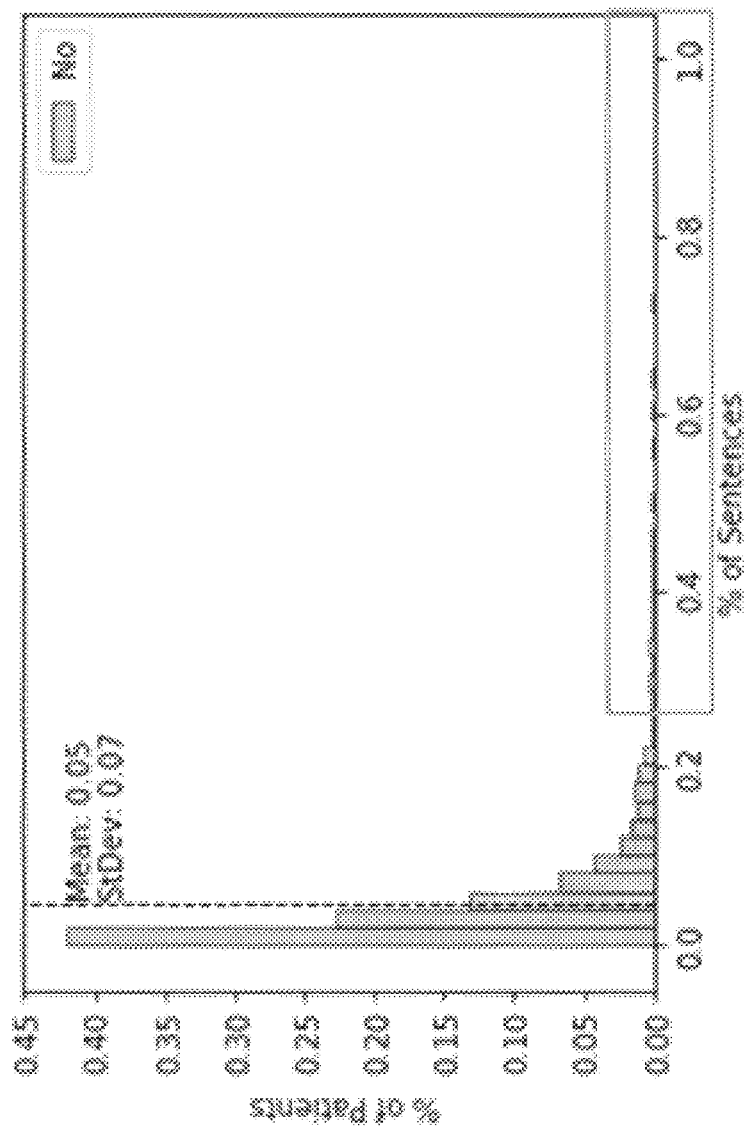

The sentiment analysis shown in FIG. 10D was also used to identify patients in the Initial PH Cohort that did not have PH according to their clinical notes. Of the 1,630 patients with clinical notes that were provided, sentiment analysis and subsequent manual review identified 35 patients in this cohort that did not have PH. An example of this semi-automated workflow is shown in FIG. 10E. Here, the distribution contains PH negative patients, resulting in a longer tail for the NO classification. For the 25 patients in this particular tail, the applications built within the computing environment containing the patient data were used to examine each mention of "pulmonary hypertension" in these patients' notes, resulting in 7 patients with PH, 2 with suspected PH, and 16 without PH. The remaining 19 patients within this cohort without PH were identified in a previous iteration.

Figure 10F:
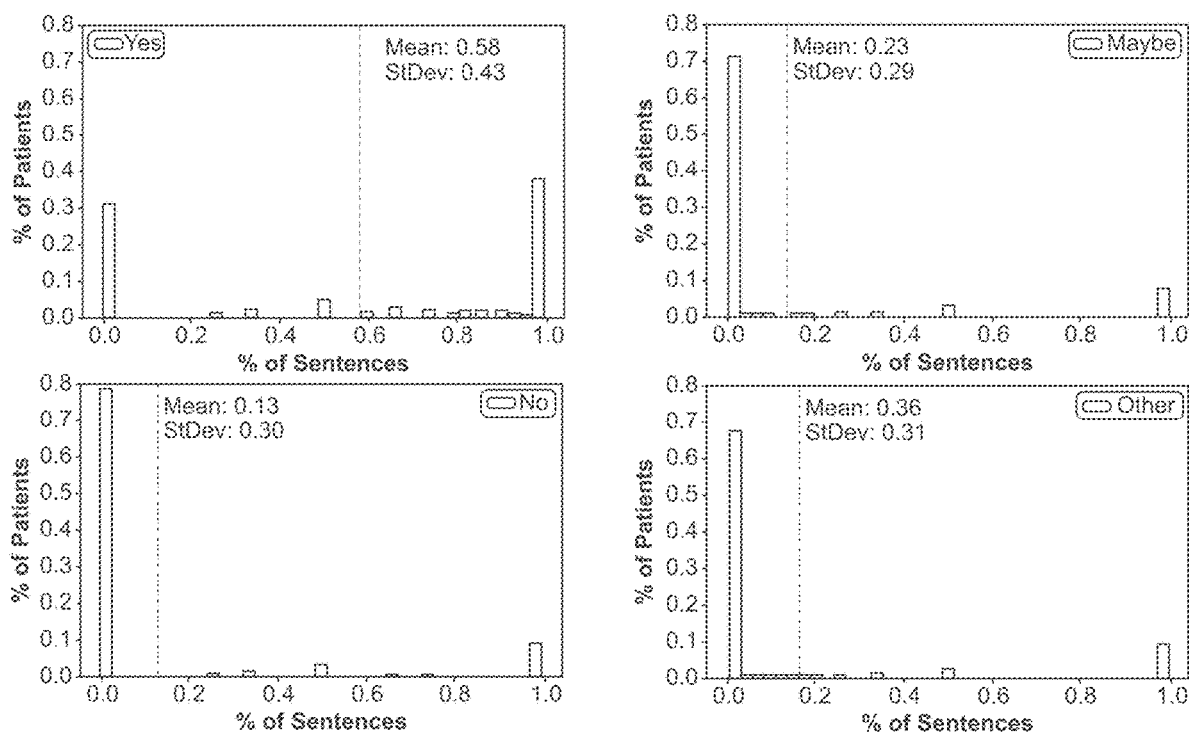

After validating the diagnosis model on the Initial PH Cohort, the model was run on sentences containing "pulmonary hypertension" for the 19,504 patients in the Potential PH Cohort. As shown in FIG. 10F, the average YES sentiment of 58% is lower than the Initial PH Cohort, but this result can primarily be accounted for by the 30% of patients without a YES sentence. Similarly, almost 80% of patients do not have a sentence with NO sentiment, meaning the PH positive control set could be increased by an order of magnitude in some embodiments.

To automate the differentiation between positive and negative PH patients in these cohorts, various logistic regression models were tested using a combination of augmented curation results and/or echocardiogram measurements, TRV and estimated right atrial pressure (RAP). Features used to describe a patient via augmented curation included the percent of sentences with Yes, No, Maybe, and Other sentiment as well as the number of PH occurrences per note. Features used for TRV and RAP included the mean, median, minimum, maximum, and standard deviation of each measurement. A positive control cohort was generated of 1556 patients from the Initial PH Cohort who had positive diagnoses and echocardiogram measurements. A negative control cohort was generated through manual curation of records for patients with TRV and RAP measurements. Models were evaluated using 10-fold cross validation and a 90:10 train-test split.

Figure 10G:
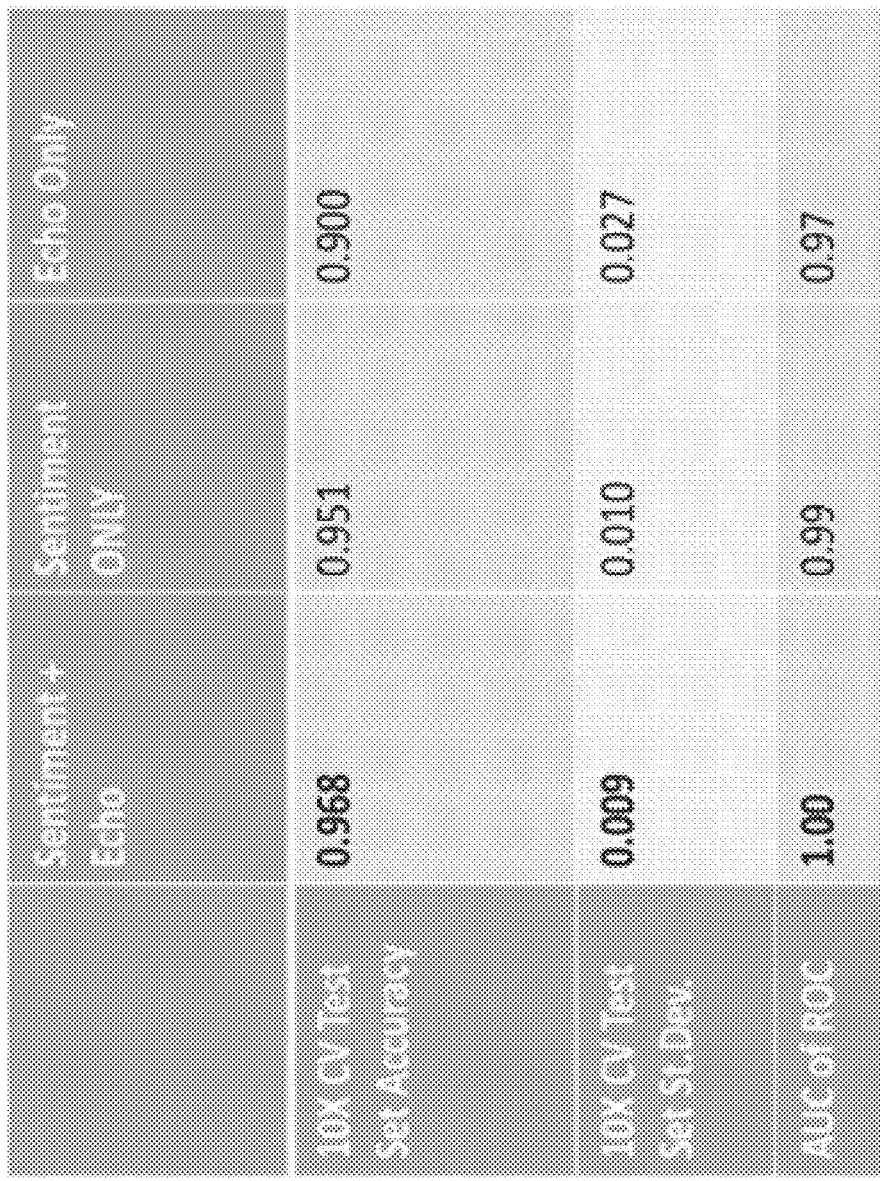
Figure 10H:
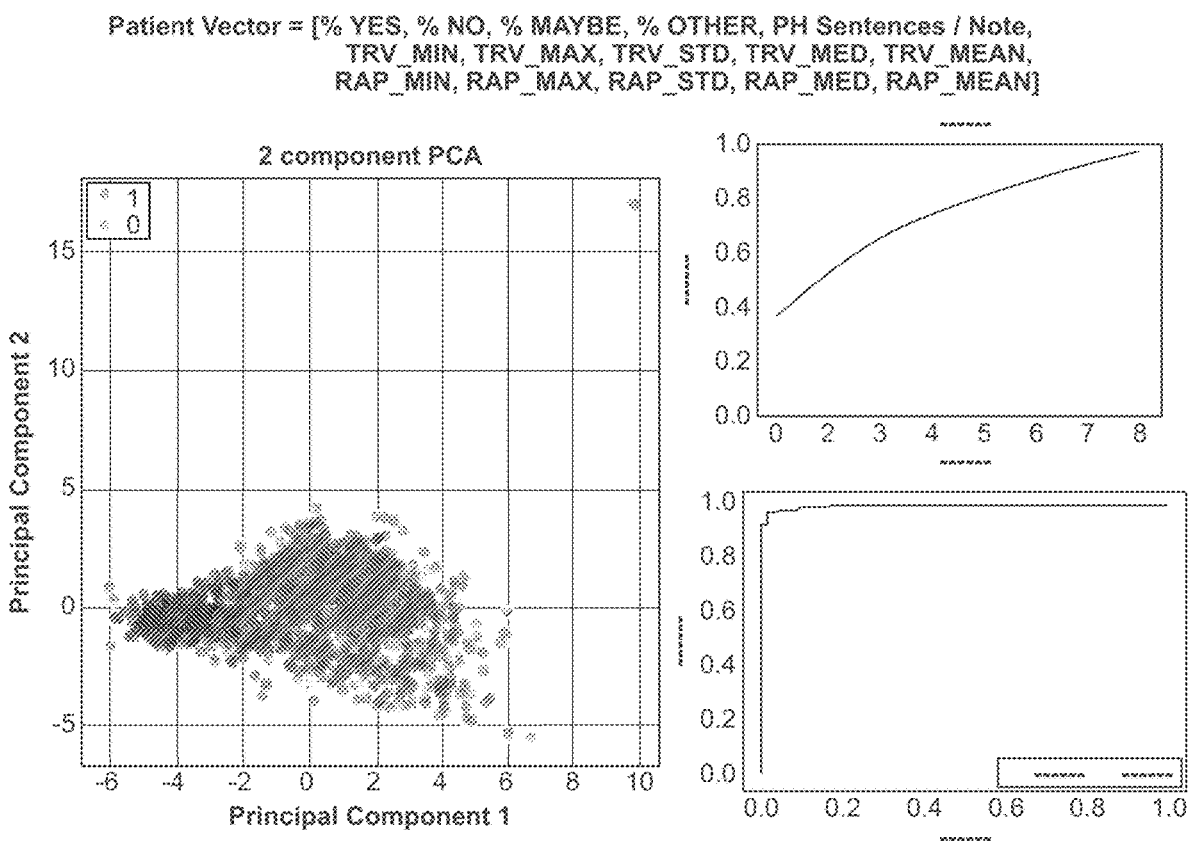

As shown in FIGS. 10G and 10H, coupling augmented curation with echocardiogram measurements performs better than either alone. Yet augmented curation performs much better than echocardiogram measurements alone. This was expected as one goal of augmented curation is to capture the physician's interpretation of the sum total of the patient's records.

Two hundred patients were randomly sampled as a hold-out set, and their records were manually curated to determine whether the patient was diagnosed with PH or not. One patient withdrew consent and was subsequently excluded. Of the remaining 199 patients, 191 were classified correctly by the logistic regression model or 95.9%.

It is to be understood that FIGS. 10A-10H are illustrative and merely describe an example of how neural network models trained on clinical notes can be coupled to the structured data from the patient health record to create patient-level classifiers for cohort selection. The feature space for these models is not limited to augmented curation coupled to echocardiograms. Additional or alternative features could be included from the unstructured text of the clinical notes, including medications given, procedures administered, and comorbidities. Similarly, echocardiogram measurements are only one source of structured data. Other sources, such as medications, procedures, and diagnosis codes could also improve classification. Even within echocardiogram procedures, TRV and RAP represent only two measurements taken, and introducing other measurements may be advantageous in some embodiments.

To train models, ECGs can be selected for one or more time windows relative to an event. In the case of PH positive cohorts, that event is either the RHC or echocardiogram (depending on the cohort definition) where the patient exceeded the mPAP or TRV threshold, respectively, i.e. the "diagnosis date". For each cohort, models were initially trained and evaluated on two different time windows: 1 month on either side of the diagnosis date (diagnosis window) and 6-18 months prior to diagnosis (pre-emptive window). In further iterations models were trained on every 6-month window preceding the diagnosis date going back to 5 year prior to diagnosis, i.e. 0-6 months, 6-12 months, etc. For negative patients, all ECGs were considered. All ECGs taken when the patient was younger than 18 years of age were excluded. For each cohort, patients were split into train (48%), test (40%), and validation (12%) sets.

Two performance metrics were used to evaluate each model: patient-wise area under the curve (AUC) and age-gender-wise AUC. Patient-wise AUC randomly sampled one ECG per patient and the mean of 50 random runs was reported. Patient-wise AUC ensure patients with more ECGs, i.e. potentially sicker patients, are not over-represented. Age-gender-wise AUC randomly sampled 4 negative ECGs for each positive ECG matched by age and gender at the time the ECG was taken. If 4 negative ECGs are not available, positive ECGs are under-sampled to maintain a 1:4 positive-negative ECG ratio. Here again, the mean of 50 random runs is reported. The advantage here is that the age and gender distributions are maintained between the positive and negative cohorts.

Figure 11A:
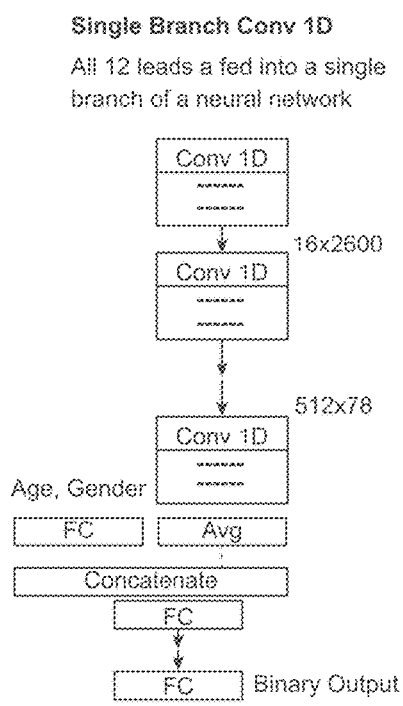
Figure 11A:
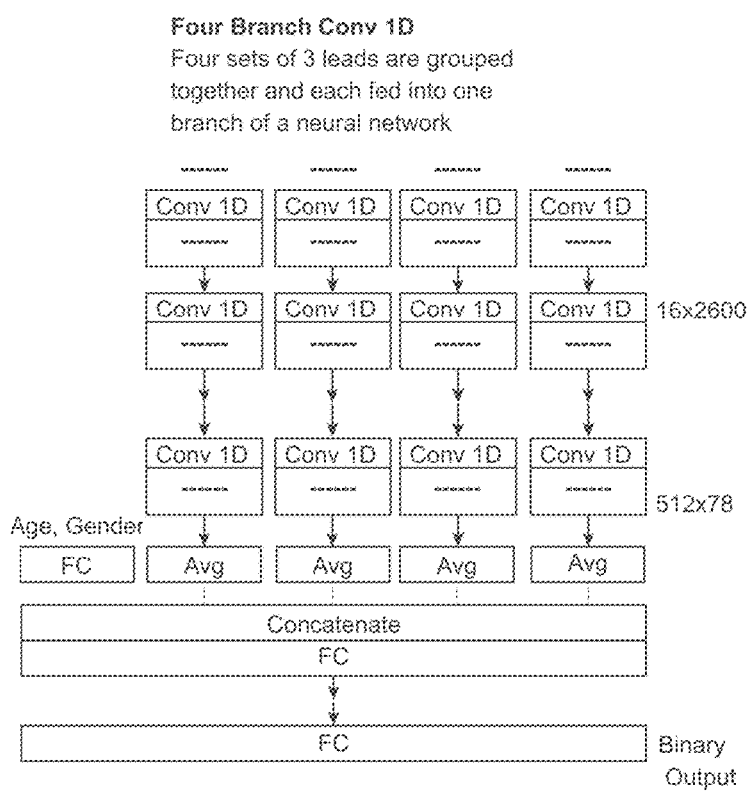
Figure 11E:
Figure 11F:
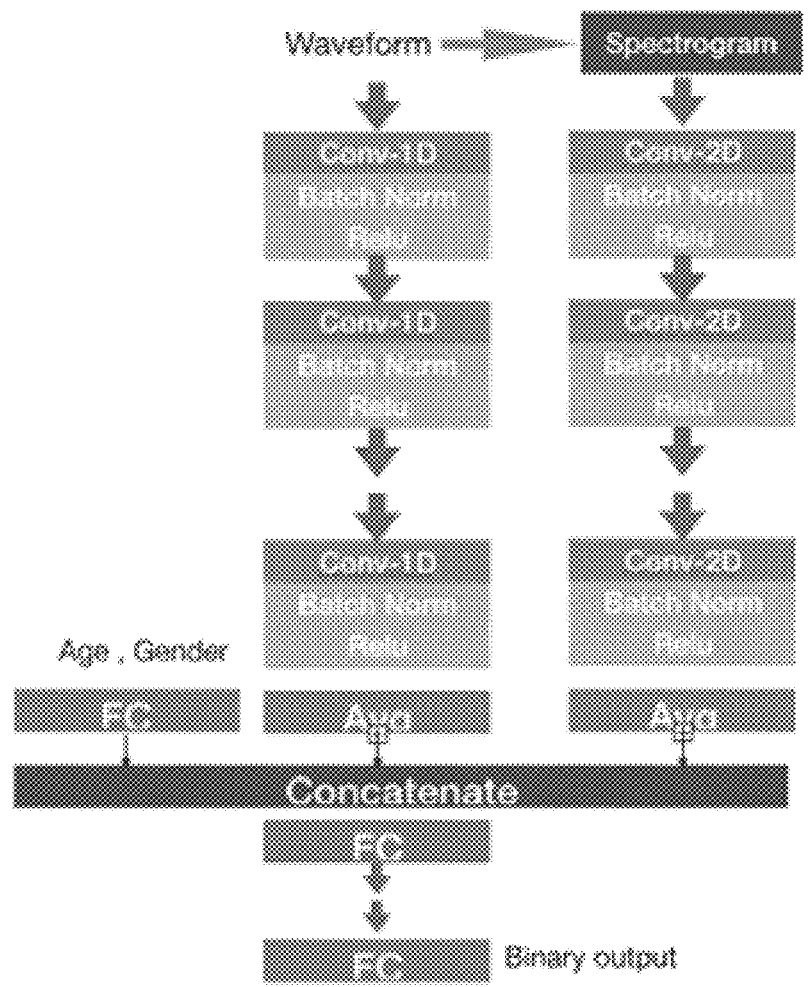
Figure 11G:
Figure 11J:
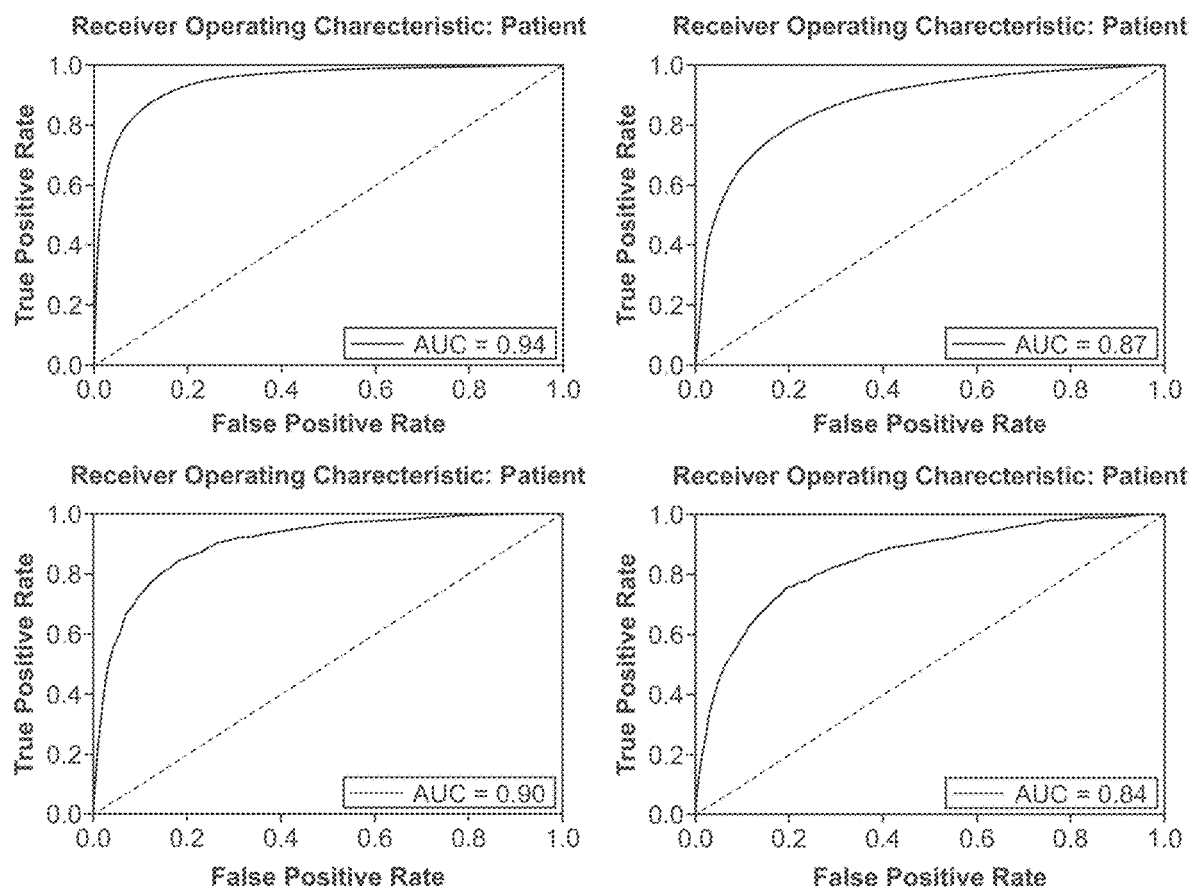
Figure 11M:
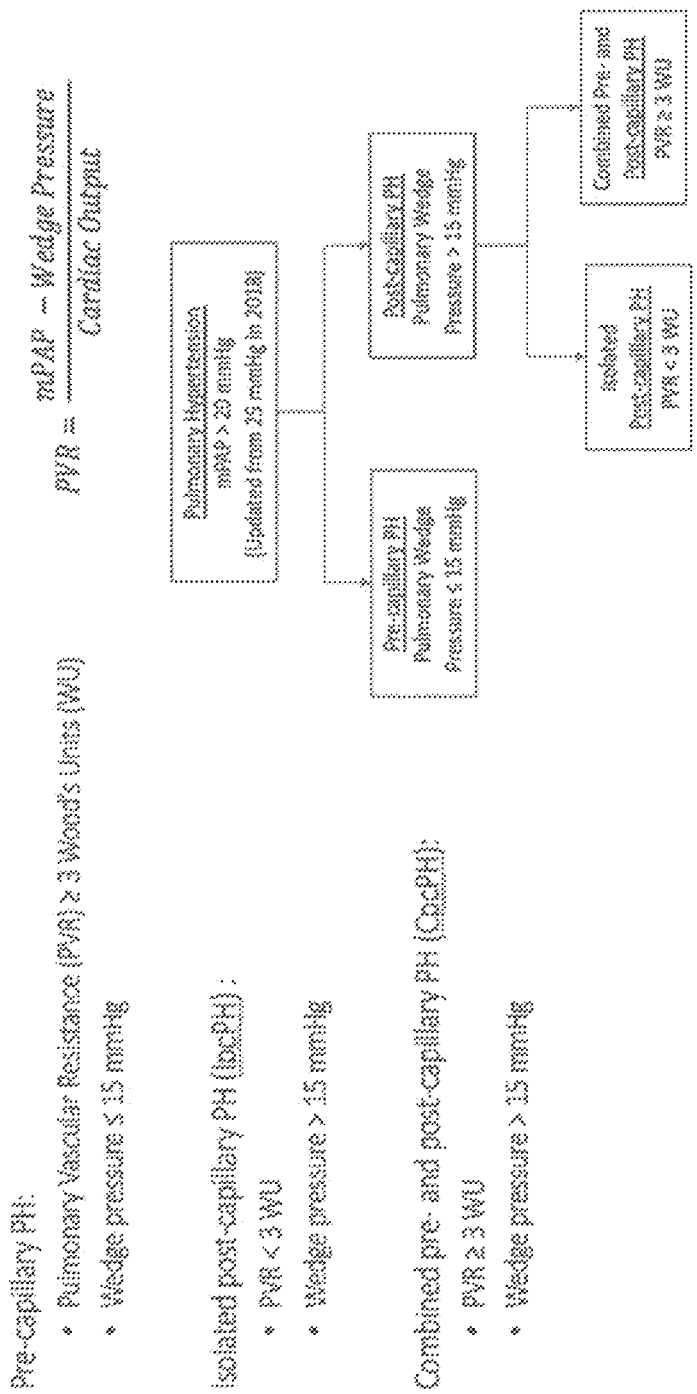
Figure 11P:
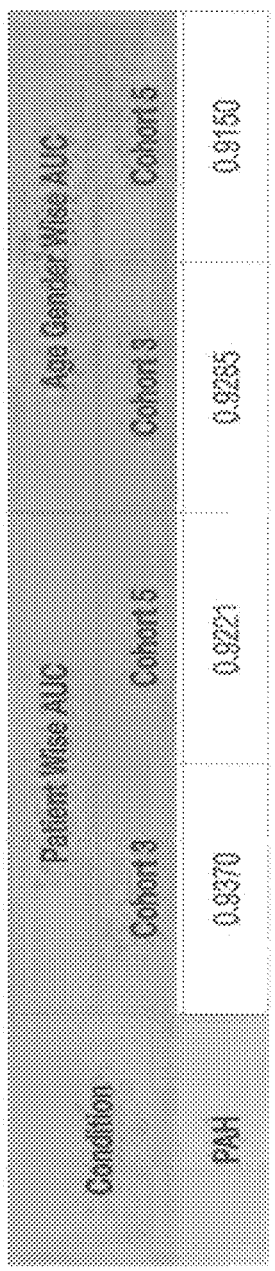
Figure 11Q:
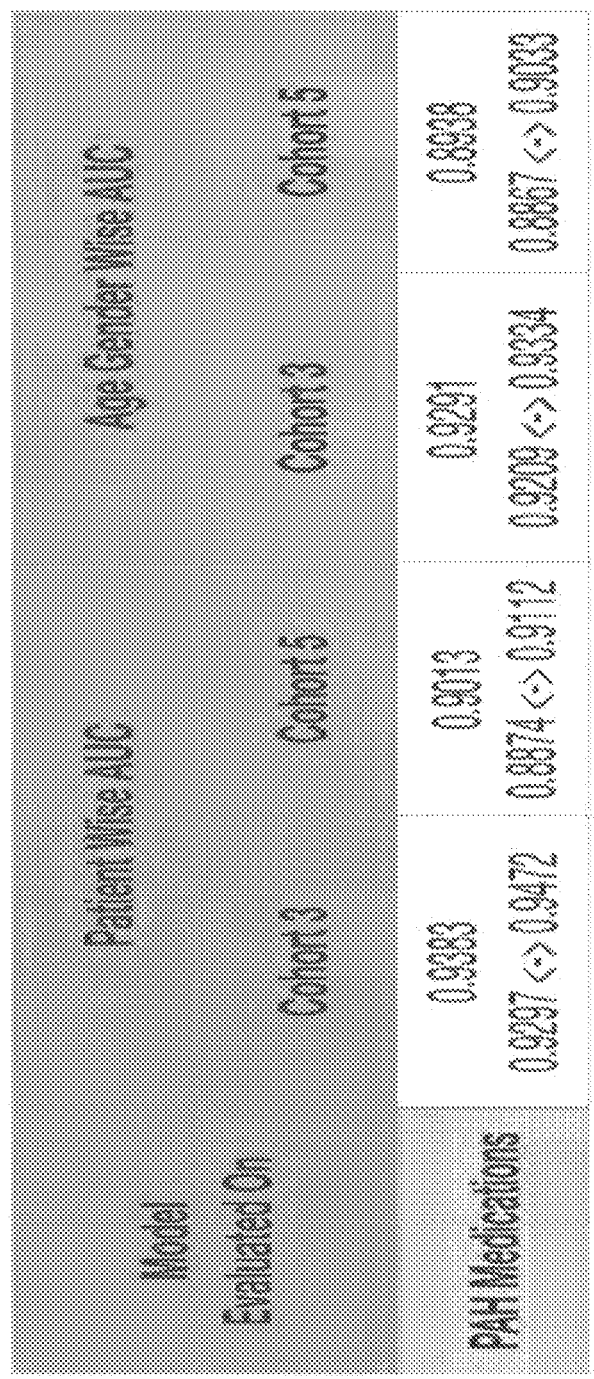
Figure 11V:
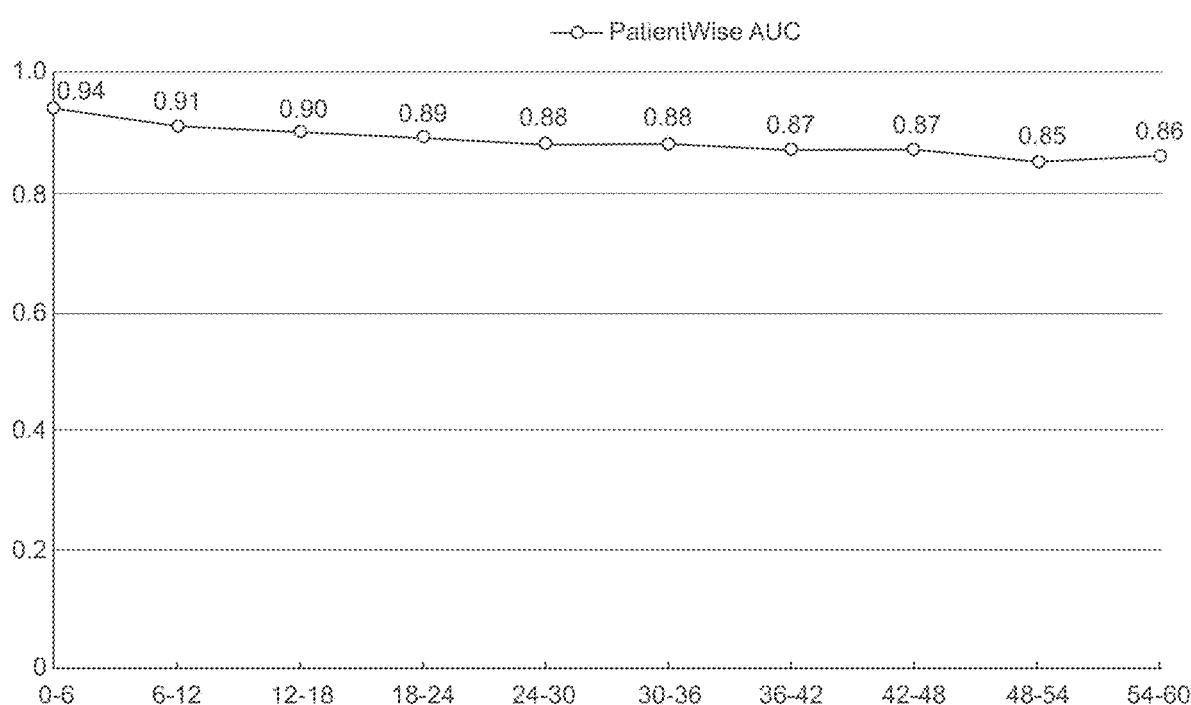

FIGS. 11A-11V are simplified diagrams summarizing the structure and performance of neural network models developed using the techniques of FIGS. 1-10H when applied to the diagnosis of pulmonary hypertension according to some embodiments. Algorithms were developed testing single-branch, four-branch, and twelve-branch 1D convolutional neural networks (CNNs), using 12-lead voltage-time signals as one input, four groups of three leads, and individual leads, respectively, as shown in FIG. 11A. Spectrogram models were also tested in which each lead of the time series signal is converted to a spectrogram, computed using a short time Fourier's transform (STFT) on time slices of 128 samples (0.256 ms), which are split into 400 bins, with the next time slice chosen after skipping 64 samples (0.128 ms). Preliminary results comparing single-branch, four-branch, and twelve-branch 1D convolutional neural networks (CNNs) with a spectrogram model are shown in FIG. 11B As shown, the single-branch 1D CNN performed better across 3 out of 4 test sets and was chosen for further development.

Probability encoded models were also tested, as described in FIG. 11C. The probability encoded models were observed to perform well in cases where the positive and negative cohorts were separated by a given threshold, e.g. Cohort 2 in which the positive cohort was defined by mPAP>21 mmHg and the negative cohort by mPAP<21 mmHg. However, the same benefit was not observed for cohorts with a separation between thresholds, e.g. Cohort 1 in which the positive cohort was defined by mPAP>25 mmHg and the negative cohort by mPAP<21 mmHg, as shown in FIG. 11D. Thus, the probability encoded models were only used for the former cohort definitions.

FIG. 11E shows the performance of models trained on ECGs from a given time window using ECGs from a different time window. As shown, we observed that a model trained on ECGs from the diagnosis window had better performance for ECGs from the pre-emptive window than a model trained on the pre-emptive window. This result indicates that training on ECGs taken when the disease is present could also be useful when developing models for early detection.

Combinations of network inputs and architectures were also tested. An illustrative example of such a combination is shown in FIG. 11F, and its measured performance is shown in FIG. 11G. For example, while the spectrogram model alone did not outperform the single-branch 1D CNN in initial tests, the combination of both inputs was able to outperform either alone in some embodiments.

Other varied parameters included age and gender as inputs, an additional 2D spectrogram, residual connections, and window size (i.e., a ten second window vs. overlapping two second windows), summarized in FIGS. 11H and 11I. An optimal model was found using a single-branch 1D CNN with residual connections and overlapping two second windows, with results for Cohort 3 summarized in FIG. 11J. Age and gender were not required as inputs and inclusion of a 2D spectrogram did not significantly increase performance.

Models were also trained and/or tested using ECGs including or excluding specific patient populations identified through both the structured and unstructured information associated with health records. Models were tested using ECGs with sinus rhythm alone or by excluding patients with pacemakers, but neither modification significantly improved performance, as shown in FIGS. 11K and 11L. As shown in FIGS. 11M and 11N, the model did perform better for pre-capillary and combined pre- and post-capillary PH patients compared to the post-capillary patients, as defined by RHC measurements, indicating that the model could be effective in the PAH population. FIG. 11O shows reference values obtained with the same models across all patients. PAH patients defined using augmented curation of the clinical notes (FIG. 11P) or through the structured medication orders (FIG. 11Q) both showed improved performance compared to the results for all PH patients. Removing chronic heart failure patients marginally improved performance (FIG. 11R) but removing heart or liver transplant patients (FIG. 11S) or patients who underwent heart surgery (FIG. 11T) did not appear to have a significant effect.

The diagnostic model trained on Cohort 3 was one of the best performing models and was used for further study, as shown in FIG. 11U. This diagnostic model was used to test ECGs from 0-5 year prior to diagnosis in 6-month windows, as shown in FIG. 11V. The diagnostic model obtained an AUC of 0.92 and 0.93 on the validation and test sets respectively, while the preliminary pre-emptive model was able to distinguish PH 6 to 18 months prior to diagnosis with an AUC of 0.85 and 0.86 on the validation and test sets respectively. Finally, ECGs taken 3-5 years prior to diagnosis did not exhibit a significant decrease in performance, with AUCs above 0.82. Ultimately, these results show a signal within ECGs useful for detecting PH. In some embodiments, neural network models for detecting this signal could be implemented in ECG machines in primary and secondary care settings to accelerate patient diagnosis and help patients receive the proper treatments they need earlier. Additionally, because this signal seems to exist 3-5 years prior to diagnosis, there may be an underlying genetic component to the disease. If so, a diagnostic coupled with a genetic panel may provide a PH diagnosis with high specificity and sensitivity.

In addition to using a single ECG for prediction, as shown in FIGS. 11A-11V the model probabilities output for multiple ECGs within a time window could be used in conjunction to classify a patient, as shown in FIGS. 12A-12D. The minimum, mean, or maximum of the probability score (calculated using a preliminary model) of multiple ECGs were used for testing. Using Cohort 3, patients with two or more ECGs taken 0-6 months prior to diagnosis, with more than 7 days between ECGs, were selected. The latter criterion was used to remove ECGs taken in an inpatient setting for acute conditions, which we found offered a marginal benefit to performance. Whether all 6-month windows were used for the negative cohort (FIG. 12A) or randomly selected a 6-month window for each negative patient (FIG. 12B) did not significantly affect the results. In both cases, using the minimum probability score improved AUC, sensitivity, and specificity, while using the maximum probability score decreased performance and the mean performed about as well as using a single ECG.

Because the ECGs used for model training were taken at rest without drug administration, patients who were challenged, either via exercise or drugs, during RHC were excluded. This exclusion criteria improved performance for single ECG models (FIG. 12C), so the criteria was also included for the positive cohort in multi-ECG models (FIG. 12D) resulting in improved performance there as well. This patient-wise exclusion was used to develop the latest version of the model, for which data can be found in FIGS. 11J, 11N, 11U, and 11V.

In addition to minimum, maximum, and mean, other methods were tested that used the probability scores (calculated using a preliminary model) from multiple ECGs to classify patients, including logistic regression and sequential scoring. Logistic regression was used to test whether an alternate function could be used to improve performance. Sequential scoring would be also be relevant in clinical use cases, in which a physician does not want to wait for 2+ ECGs to be taken. Using this method, each additional ECG taken would be accounted for by the model in sequence at the time it is acquired, but there would be no minimum number of ECGs required to limit the physician's decision-making timeline.

Although the previous methods have used multiple ECGs by utilizing the output probability score from each ECGs run separately through the model, this is merely illustrative, and various alternatives are contemplated. For example, in some embodiments the neural network models may be trained using multiple ECGs as inputs to the model.

Figure 13:
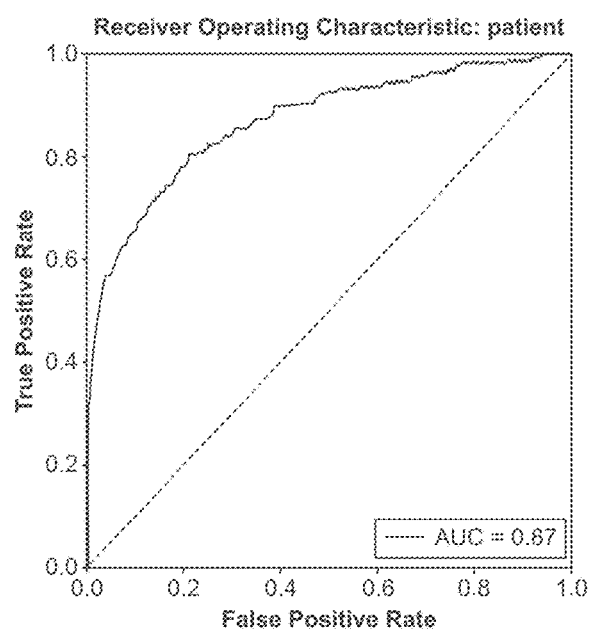
FIG. 13 is a simplified diagram showing experimental data associated with the techniques of FIGS. 1-9 applied to the diagnosis of AL amyloidosis according to some embodiments; Various objectives, features, and advantages of the disclosed subject matter can be more fully appreciated with reference to the following detailed description of the disclosed subject matter when considered in connection with the following drawings, in which like reference numerals identify like elements.

FIG. 13 is a simplified diagram showing experimental data associated with the techniques of FIGS. 1-9 applied to the diagnosis of AL amyloidosis according to some embodiments. AL amyloidosis is the most common type of systemic amyloidosis. Patients with AL amyloidosis have an underlying disorder in which there is overproduction of light chains that can form amyloid deposits in various tissues, particularly the heart, kidneys, lungs, skin, nerves, and blood. AL amyloidosis most commonly arises from clonal bone marrow plasma cells, explaining why the condition is reported to be found in approximately 15% of multiple myeloma patients, but in some cases other clonal B-cell disorders also secrete amyloidogenic light chains, e.g. lymphoplasmacytic lymphoma, Waldenstrom's macroglobulinemia, chronic lymphocytic leukemia, and follicular lymphoma. Amyloid deposits can form in almost any tissue of the body. Therefore, the symptoms and signs of the disease can vary greatly and are not specific to AL amyloidosis. Since amyloidosis is rare and the symptoms are nonspecific, missed or delayed diagnosis is common. Prior studies have found that approximately 40% of AL amyloidosis patients were not diagnosed until more than 1 year after the onset of initial symptoms. Thus, early diagnosis would improve treatment efficacy and overall survival and is an opportune area for early detection algorithms.

For a preliminary study, patients were identified from a subset of 700 k patients who had AL amyloidosis identified via augmented curation in their clinical notes (ALA=1264 patients) as a positive cohort. Next, patients with multiple myeloma (MM) ICD codes (two codes separated by at least 90 days) but no ALA diagnosis in their notes (MM=2471 patients) were identified. Lab measurements enriched in the ALA vs. MM cohorts were then computed. These lab tests included markers of organ function and damage, including: estimated glomerular filtration rate (eGFR), N-type brain natriuretic peptide (NTproBNP), cardiac troponin T (cTnT), Factor Xa levels (FXa), thyroid stimulating hormone (TSH), and serum alkaline phosphatase (ALP). Abnormal ranges for these tests were identified based on literature examining how these lab values change in AL amyloidosis. A condition that the MM cohort should never have an abnormal lab test (of the labs listed) was applied. This cohort became the negative cohort (NEG=798 patients). A preliminary model was trained to classify ALA vs. NEG using ECGs taken 1 month on either side of the diagnosis date (ALA or MM, respectively); the resulting AUC, sensitivity, and specificity were 0.87, 77.0%, and 81.0%, respectively (FIG. 2), which is promising given the small preliminary cohort sizes relative to the PH models. By refining the cohorts and increasing the sizes of those cohorts, this performance is expected to increase further.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter, which is limited only by the claims which follow.

What is claimed is:

1. A method for diagnosing a health condition based on patient time series data, wherein the method comprises:
   receiving, using one or more hardware processors, patient time series data, wherein the patient time series data comprises an electrocardiogram (ECG) waveform;
   identifying, using the one or more hardware processors, a training set of health records, wherein:
      the training set of health records comprises health records of patients who have been diagnosed with a health condition of interest and training data including ECG waveforms of the patients correlated to the health condition of interest; and
      identifying the training set of health records comprises identifying one or more cohorts of the patients;
   training, using the one or more hardware processors, a plurality of neural network models for each cohort of the patients using the training set of health records;
   selecting, using the one or more hardware processors, one or more highest performing models from the plurality of trained neural network models;
   executing, using the one or more hardware processors, the one or more highest performing models as a function of the patient time series data, wherein executing the one or more highest performing models comprises:
      preprocessing the time series data, wherein preprocessing the time series data comprises:
         extracting one or more discrete metrics as a function of the time series data, wherein the one or more discrete metrics comprises an interval of an ECG waveform; and
   predicting, using the one or more hardware processors, a health condition as a function of the patient time series data, the interval of the ECG waveform, and the one or more highest performing models.

2. The method of claim 1, wherein the interval of the ECG waveform comprises a QT interval.

3. The method of claim 2, wherein the training set of health records further comprises ethnicity of patients.

4. The method of claim 3, wherein the training set of health records further comprises QT intervals correlated with the patients who have been diagnosed with the health condition of interest.

5. The method of claim 4, further comprising recommending, using the one or more hardware processors, an intervention as a function of the predicted heart condition.

6. The method of claim 1, further comprising:
   obtaining, using the one or more hardware processors, the training set of health records for each cohort of the one or more cohorts of the patients from a corpus of health records using a search query.

7. The method of claim 1, wherein the training set of health records comprises exemplary pre-emptive time series data.

8. The method of claim 1, further comprising:
   receiving, using the one or more hardware processors, patient information as an input data for the one or more highest performing models, wherein the patient information comprises ethnicity of the patient.

9. The method of claim 8, further comprising selecting, suing the one or more hardware processors, the one or more highest performing models from the plurality of trained neural network models as a function of the patient information.

10. The method of claim 1, further comprising:
    outputting, using the one or more hardware processors and the one or more highest performing models, a numerical score of a risk of having the health condition.

11. A system for diagnosing a health condition based on patient time series data, wherein the system comprises:
    a non-transitory memory; and
    one or more hardware processors configured to read instructions from the non-transitory that, when executed, cause the one or more hardware processors to perform operations comprising:
receive patient time series data, wherein the patient time series data comprises an electrocardiogram (ECG) waveform;
identify a training set of health records, wherein:
- the training set of health records comprises health records of patients who have been diagnosed with a health condition of interest and training data including ECG waveforms of the patients correlated to the health condition of interest; and
- identifying the training set of health records comprises identifying one or more cohorts of the patients;

train a plurality of neural network models for each cohort of the patients using the training set of health records;
select one or more highest performing models from the plurality of trained neural network models;
execute the one or more highest performing models as a function of the patient time series data, wherein executing the one or more highest performing models comprises:
- preprocessing the time series data, wherein preprocessing the time series data comprises:
  - extracting one or more discrete metrics as a function of the time series data, wherein the one or more discrete metrics comprises an interval of an ECG waveform; and predict a health condition as a function of the patient time series data, the interval o the ECG wave form, and the one or more highest performing models.

12. The system of claim 11, wherein the interval of the ECG waveform comprises a QT interval.

13. The system of claim 12, wherein the training set of health records further comprises ethnicity of patients.

14. The system of claim 13, wherein the training set of health records further comprises QT intervals correlated with the patients who have been diagnosed with the health condition of interest.

15. The system of claim 14, wherein the one or more hardware processors is further configured to recommend an intervention as a function of the predicted heart condition.

16. The system of claim 11, wherein the one or more hardware processors is further configured to obtain the training set of health records for each cohort of the one or more cohorts of the patients from a corpus of health records using a search query.

17. The system of claim 11, wherein the one or more hardware processors is further configured to output a numerical score of a risk of having the health condition using the one or more highest performing models.

18. The system of claim 11, wherein the one or more hardware processors is further configured to convert the time series data to a spectrogram representation.

19. The system of claim 18, wherein the one or more hardware processors is further configured to select the one or more highest performing models from the plurality of trained neural network models as a function of the patient information.

20. The system of claim 11, wherein the one or more processors is further configured to output, using the one or more highest performing models, a numerical score of a risk of having the health condition.

* * * * *